United States Patent [19]

Shamanin et al.

[11] Patent Number: 6,025,163
[45] Date of Patent: Feb. 15, 2000

[54] DNA CODING FOR A PEPTIDE OF A PAPILLOMA VIRUS MAIN CAPSIDE PROTEIN AND USE THEREOF

[75] Inventors: Vladimir Shamanin, Heidelberg; Ethel-Michele De Villiers-Zur Hausen, Hirschberg, both of Germany; Irene Leigh, London, United Kingdom; Harald Zur Hausen, Hirschberg, Germany

[73] Assignee: Deutsches Krebsforschungzentrum Stiftung Des Offentlichen Rechts, Germany

[21] Appl. No.: 08/578,634

[22] PCT Filed: May 4, 1995

[86] PCT No.: PCT/EP95/01697

§ 371 Date: Jun. 14, 1996

§ 102(e) Date: Jun. 14, 1996

[87] PCT Pub. No.: WO95/30754

PCT Pub. Date: Nov. 16, 1995

[30] Foreign Application Priority Data

May 4, 1994 [DE] Germany ............... 44 15 743

[51] Int. Cl.[7] .............. C12P 21/06; C12N 15/00
[52] U.S. Cl. ............ 435/69.3; 435/69.1; 435/252.3; 435/320.1; 530/350; 530/403; 536/23.72; 424/199.1; 424/204.1
[58] Field of Search ............... 435/69.3, 69.1, 435/252.3, 320.1; 530/350, 403; 536/23.72; 424/199.1, 204.1

[56] References Cited

FOREIGN PATENT DOCUMENTS

| | | |
|---|---|---|
| WO9118294 | 2/1991 | WIPO . |
| WO9302184 | 5/1993 | WIPO . |
| WO9400152 | 1/1994 | WIPO . |
| Wo9405792 | 3/1994 | WIPO . |
| WO9420137 | 9/1994 | WIPO . |

OTHER PUBLICATIONS

Shamanin, et al., Sep. 1994, "Specific types of human papillomavirus found in benign proliferations and carcinomas of the skin in immunosuppressed patients, " *Cancer Research* 17:4610–4613 .

Zur Hausen, 1989, *Cancer Research* 49:4677–4681.

Zur Hausen, 1976, *Cancer Research* 36:530.

Syrjänen, 1980, *Lung* 158;131–142.

Kirnbauer, et al., 1993, *J. Virology* 6929–6936.

Hagensee, et al., 1993, *J. Virology* 315–322.

Rose et al. 1993, J. of Virology, vol. 76, No. 4, pp. 1936–1944, Apr. 1993.

Tomita et al. 1987, J. of Virology, vol. 61, No. 8, pp. 2389–2394, Aug.1987.

Tomita et al. 1987, Virology, vol. 158, pp. 8–14, 1987.

Volpers et al. 1991, Virology, vol. 181, pp. 419–423, 1991.

*Primary Examiner*—Chris Eisenschenk
*Assistant Examiner*—Ali R. Salimi
*Attorney, Agent, or Firm*—Pennie & Edmonds LLP

[57] ABSTRACT

This invention relates to a DNA encoding a peptide of a papilloma virus major capsid protein. Furthermore, this invention deals with a papilloma virus genome containing such a DNA. In addition, this invention concerns proteins encoded by the papilloma virus genome and virus-like particles as well as antibodies directed thereagainst and the use thereof and the use thereof in diagnosis, treatment and vaccination.

27 Claims, 19 Drawing Sheets

FIG. 1-A

```
        GGTAGAGGACAGCCATTAGGCGTGGGGTTAAGTGGACACCCTCTGTATAACAAACTGAAT
      1 ----------+----------+----------+----------+----------+----------+  60
        CCATCTCCTGTCGGTAATCCGCACCCCAATTCACCTGTGGGAGACATATTGTTTGACTTA a         G  R  G  Q  P  L  G  V  G  L  S  G  H  P  L  Y  N  K  L  N       -

GACACTGAAAACTCCAACATTGCACATGCTGACAATAGTCCTGACTCCCGGGACAACATT
     61 ----------+----------+----------+----------+----------+----------+ 120
        CTGTGACTTTTGAGGTTGTAACGTGTACGACTGTTATCAGGACTGAGGGCCCTGTTGTAA a         D  T  E  N  S  N  I  A  H  A  D  N  S  P  D  S  R  D  N  I       -

TCTGTTGACTGTAAGCAAACACAACTGTGCATACTGGGCTGTACGCCCCCCATGGGGGAA
    121 ----------+----------+----------+----------+----------+----------+ 180
        AGACAACTGACATTCGTTTGTGTTGACACGTATGACCCGACATGCGGGGGGTACCCCCTT a         S  V  D  C  K  Q  T  Q  L  C  I  L  G  C  T  P  P  M  G  E       -

TACTGGGGTAAGGGTACCCCTTGTGCACGTACTAATACTACCCCAGGAGACTGTCCTCCC
    181 ----------+----------+----------+----------+----------+----------+ 240
        ATGACCCCATTCCCATGGGGAACACGTGCATGATTATGATGGGGTCCTCTGACAGGAGGG a         Y  W  G  K  G  T  P  C  A  R  T  N  T  T  P  G  D  C  P  P       -

TTGGAGTTAATGACATCTTATATTCAGGATGGCGACATGGTGGATACCGGGTATGGTGCC
    241 ----------+----------+----------+----------+----------+----------+ 300
        AACCTCAATTACTGTAGAATATAAGTCCTACCGCTGTACCACCTATGGCCCATACCACGG a         L  E  L  M  T  S  Y  I  Q  D  G  D  M  V  D  T  G  Y  G  A       -

ATGGACTTTACTGCCCTGCAATTTAATAAGTCTGACGTGCCCCTTGATATTTGCCAGTCT
    301 ----------+----------+----------+----------+----------+----------+ 360
        TACCTGAAATGACGGGACGTTAAATTATTCAGACTGCACGGGGAACTATAAACGGTCAGA a         M  D  F  T  A  L  Q  F  N  K  S  D  V  P  L  D  I  C  Q  S       -

ATTTGCAAATATCCCGATTATTTGGGCATGGCTGCCGACCCGTATGGCGATAGCATGTTC
    361 ----------+----------+----------+----------+----------+----------+ 420
        TAAACGTTTATAGGGCTAATAAACCCGTACCGACGGCTGGGCATACCGCTATCGTACAAG a         I  C  K  Y  P  D  Y  L  G  M  A  A  D  P  Y  G  D  S  M  F       -

TTTTTCCTCCGTCGGGAACAACTGTTTGCCAGACACTTTTTCAATCGTGCGGGTGATGTT
    421 ----------+----------+----------+----------+----------+----------+ 480
        AAAAAGGAGGCAGCCCTTGTTGACAAACGGTCTGTGAAAAAGTTAGCACGCCCACTACAA a         F  F  L  R  R  E  Q  L  F  A  R  H  F  F  N  R  A  G  D  V       -
```

FIG. 1-B

```
         GGAGACAAAATTCCAGAATCTTTGTACCTCAAAGGGAGTAGCGGGCGTGAGACTCCCGGC
    481  ----------+----------+----------+----------+----------+----------+  540
         CCTCTGTTTTAAGGTCTTAGAAACATGGAGTTTCCCTCATCGCCCGCACTCTGAGGGCCG a        G  D  K  I  P  E  S  L  Y  L  K  G  S  S  G  R  E  T  P  G     -

AGTGCTATATACAGCCCCACACCCAGTGGGTCTATGGTGACCTCTGAGGCACAAATATTC
    541  ----------+----------+----------+----------+----------+----------+  600
         TCACGATATATGTCGGGGTGTGGGTCACCCAGATACCACTGGAGACTCCGTGTTTATAAG a        S  A  I  Y  S  P  T  P  S  G  S  M  V  T  S  E  A  Q  I  F     -

AATAAGTCTTACTGGCTACAGCAAGCTCAAGGCCAAAATAACGGTAT
    601  ----------+----------+----------+----------+-------  647
         TTATTCAGAATGACCGATGTCGTTCGAGTTCCGGTTTTATTGCCATA a        N  K  S  Y  W  L  Q  Q  A  Q  G  Q  N  N  G       -
```

FIG. 2-A

```
    TCAAGAGGACACCCATTAGGAGTAGGGTCTACAGGTCATCCCCTATTTAATAAAGTGAAG
  1 ----------+----------+----------+----------+----------+----------+  60
    AGTTCTCCTGTGCGTAATCCTCATCCCAGATGTCCAGTAGGGGATAAATTATTTCACTTC a   S  R  G  H  P  L  G  V  G  S  T  G  H  P  L  F  N  K  V  K    -

GATACGGAAAATGCTAATAATTATATAGTAACATCTAAGGATGATAGGCAGGACACCTCA
 61 ----------+----------+----------+----------+----------+----------+ 120
    CTATGCCTTTTACGATTATTAATATATCATTGTAGATTCCTACTATCCGTCCTGTGGAGT a   D  T  E  N  A  N  N  Y  I  V  T  S  K  D  D  R  Q  D  T  S    -

TTTGATCCTAAACAGGTTCAAATGTTTATTATTGGCTGCGCACCGTGCATAGGTGAGCAC
121 ----------+----------+----------+----------+----------+----------+ 180
    AAACTAGGATTTGTCCAAGTTTACAAATAATAACCGACGCGTGGCACGTATCCACTCGTG a   F  D  P  K  Q  V  Q  M  F  I  I  G  C  A  P  C  I  G  E  H    -

TGGGATGCAGCCAAGCCCTGTGATGCTGACAGAGGGGTAGGCAAATGTCCACCTTTGGAA
181 ----------+----------+----------+----------+----------+----------+ 240
    ACCCTACGTCGGTTCGGGACACTACGACTGTCTCCCCATCCGTTTACAGGTGGAAACCTT a   W  D  A  A  K  P  C  D  A  D  R  G  V  G  K  C  P  P  L  E    -

CTGGTAAATACTGTAATAGAAGATGGAGATATGGTGGATATAGGTTTTGGAAATATAAAT
241 ----------+----------+----------+----------+----------+----------+ 300
    GACCATTTATGACATTATCTTCTACCTCTATACCACCTATATCCAAAACCTTTATATTTA a   L  V  N  T  V  I  E  D  G  D  M  V  D  I  G  F  G  N  I  N    -

AATAAAACCCTGTCAGCAAATAAGTCAGATGTCAGTTTAGATATAGTTAATAATATTTGT
301 ----------+----------+----------+----------+----------+----------+ 360
    TTATTTTGGGACAGTCGTTTATTCAGTCTACAGTCAAATCTATATCAATTATTATAAACA a   N  K  T  L  S  A  N  K  S  D  V  S  L  D  I  V  N  N  I  C    -

AAGTATCCAGACTTTTTAAAAATGGCCAATGACATATATGGAGACTCCTGTTTTTTTTAT
361 ----------+----------+----------+----------+----------+----------+ 420
    TTCATAGGTCTGAAAAATTTTTACCGGTTACTGTATATACCTCTGAGGACAAAAAAAATA a   K  Y  P  D  F  L  K  M  A  N  D  I  Y  G  D  S  C  F  F  Y    -

GCTAGACGGGAGCAATGTTATGCTAGACATTTTTTTGTTAGAGGAGGTAATGTAGGAGAT
421 ----------+----------+----------+----------+----------+----------+ 480
    CGATCTGCCCTCGTTACAATACGATCTGTAAAAAAACAATCTCCTCCATTACATCCTCTA a   A  R  R  E  Q  C  Y  A  R  H  F  F  V  R  G  G  N  V  G  D    -
```

FIG. 2-B

```
      GCTATTCCTGATGCTGCAGTGGGTCAGGACAATAACTTTGTGTTGCCTGCAGCTGTTGGA
  481 ---------+---------+---------+---------+---------+---------+ 540
      CGATAAGGACTACGACGTCACCCAGTCCTGTTATTGAAACACAACGGACGTCGACAACCT
``` a     A   I   P   D   A   A   V   G   Q   D   N   N   F   V   L   P   A   A   V   G    -

```
      CAGGCCCAAAACACTTTGGGTAGCTCTATTTACGTGCCTACCGTTAGTGGTTCTTTGGTA
  541 ---------+---------+---------+---------+---------+---------+ 600
      GTCCGGGTTTTGTGAAACCCATCGAGATAAATGCACGGATGGCAATCACCAAGAAACCAT
``` a     Q   A   Q   N   T   L   G   S   S   I   Y   V   P   T   V   S   G   S   L   V    -

```
      TCCACAGATGCACAATTATTTAATAGGCCCTTTTGGCTACAACGAGCACAGGGTCATAAT
  601 ---------+---------+---------+---------+---------+---------+ 660
      AGGTGTCTACGTGTTAATAAATTATCCGGGAAAACCGATGTTGCTCGTGTCCCAGTATTA
``` a     S   T   D   A   Q   L   F   N   R   P   F   W   L   Q   R   A   Q   G   H   N    -

```
      AACGGTAT
  661 -------- 668
      TTGCCATA
```

FIG. 3-A

```
    TCTAGGGGGCAACCCTTGGGGGTAGGTTCTACAGGCCATCCTTTGTTCAATAAAGTAAAG
  1 ----------+----------+----------+----------+----------+----------+  60
    AGATCCCCCGTTGGGAACCCCCATCCAAGATGTCCGGTAGGAAACAAGTTATTTCATTTC
``` a     S   R   G   Q   P   L   G   V   G   S   T   G   H   P   L   F   N   K   V   K    -

```
    GATACTGAAAATTCAAATAATTATATAACAATGTCTAAAGATGATAGGCAGGACACCTCG
 61 ----------+----------+----------+----------+----------+----------+ 120
    CTATGACTTTTAAGTTTATTAATATATTGTTACAGATTTCTACTATCCGTCCTGTGGAGC
``` a     D   T   E   N   S   N   N   Y   I   T   M   S   K   D   D   R   Q   D   T   S    -

```
    TTTGACCCTAAGCAGGTTCAAATGTTTATTATTGGCTGTGCACCTTGTATAGGGGAGCAC
121 ----------+----------+----------+----------+----------+----------+ 180
    AAACTGGGATTCGTCCAAGTTTACAAATAATAACCGACACGTGGAACATATCCCCTCGTG
``` a     F   D   P   K   Q   V   Q   M   F   I   I   G   C   A   P   C   I   G   E   H    -

```
    TGGGATGCTGCCAAACCCTGTGACGCTGACAAAGGAGACGGTAAATGTCCACCTTTAGAA
181 ----------+----------+----------+----------+----------+----------+ 240
    ACCCTACGACGGTTTGGGACACTGCGACTGTTTCCTCTGCCATTTACAGGTGGAAATCTT
``` a     W   D   A   A   K   P   C   D   A   D   K   G   D   G   K   C   P   P   L   E    -

```
    TTAGTAAATACAGTTATTGAGGATGGGGATATGGTGGATATAGGTTTTGGTAACATAAAT
241 ----------+----------+----------+----------+----------+----------+ 300
    AATCATTTATGTCAATAACTCCTACCCCTATACCACCTATATCCAAAACCATTGTATTTA
``` a     L   V   N   T   V   I   E   D   G   D   M   V   D   I   G   F   G   N   I   N    -

```
    AATAAAACCTTGTCAGCAAATAAATCAGATGTCAGTTTGGATATAGTTAATAACATTTGT
301 ----------+----------+----------+----------+----------+----------+ 360
    TTATTTTGGAACAGTCGTTTATTTAGTCTACAGTCAAACCTATATCAATTATTGTAAACA
``` a     N   K   T   L   S   A   N   K   S   D   V   S   L   D   I   V   N   N   I   C    -

```
    AAGTATCCAGACTTCCTTAAAATGGCCAATGACATATATGGGGACTCCTGTTTTTTTTAT
361 ----------+----------+----------+----------+----------+----------+ 420
    TTCATAGGTCTGAAGGAATTTTACCGGTTACTGTATATACCCCTGAGGACAAAAAAAATA
``` a     K   Y   P   D   F   L   K   M   A   N   D   I   Y   G   D   S   C   F   F   Y    -

```
    GCCAGGCGGGAACAATGTTATGCTAGACACTTTTTTGTTAGGGGAGGCAATGTAGGCGAT
421 ----------+----------+----------+----------+----------+----------+ 480
    CGGTCCGCCCTTGTTACAATACGATCTGTGAAAAAACAATCCCCTCCGTTACATCCGCTA
``` a     A   R   R   E   Q   C   Y   A   R   H   F   F   V   R   G   G   N   V   G   D    -

FIG. 3-B

```
        CGAATTCCTAATGCTGCAGTGGGTCAGGACAATAATTTTATGTTACCTGCAGCCGCTGGG
    481 ---------+---------+---------+---------+---------+---------+ 540
        GCTTAAGGATTACGACGTCACCCAGTCCTGTTATTAAAATACAATGGACGTCGGCGACCC a       R  I  P  N  A  A  V  G  Q  D  N  N  F  M  L  P  A  A  A  G   -

CAGGCTCAAAACACTTTGGGCAACTCTATTTATGTTCCCACGGTCAGTGGTTCTTTGGTG
    541 ---------+---------+---------+---------+---------+---------+ 600
        GTCCGAGTTTTGTGAAACCCGTTGAGATAAATACAAGGGTGCCAGTCACCAAGAAACCAC a       Q  A  Q  N  T  L  G  N  S  I  Y  V  P  T  V  S  G  S  L  V   -

TCCACAGATGCTCAATTATTTAACAGGCCATTTTGGCTGCAACGAGCACAAGGTCACAAC
    601 ---------+---------+---------+---------+---------+---------+ 660
        AGGTGTCTACGAGTTAATAAATTGTCCGGTAAAACCGACGTTGCTCGTGTTCCAGTGTTG a       S  T  D  A  Q  L  F  N  R  P  F  W  L  Q  R  A  Q  G  H  N   -

```
    GGAAGTGGTCTTCCATTAGGCATAGGCAGCAGTGGTCACCCTCTGTTTAACAAGGTAAAT
  1 ---------+---------+---------+---------+---------+---------+  60
    CCTTCACCAGAAGGTAATCCGTATCCGTCGTCACCAGTGGGAGACAAATTGTTCCATTTA
``` a       G  S  G  L  P  L  G  I  G  S  S  G  H  P  L  F  N  K  V  N       -

```
    GATACAGAAAATGGCAACACATATAAAGGGACAACTAAAGATGATAGACAAAACATTTCA
 61 ---------+---------+---------+---------+---------+---------+ 120
    CTATGTCTTTTACCGTTGTGTATATTTCCCTGTTGATTTCTACTATCTGTTTTGTAAAGT
``` a       D  T  E  N  G  N  T  Y  K  G  T  T  K  D  D  R  Q  N  I  S       -

```
    TTTGATCCTAAACAATTACAGATGTTTATAATTGGCTGTACACCATGTATTGGTGAACAT
121 ---------+---------+---------+---------+---------+---------+ 180
    AAACTAGGATTTGTTAATGTCTACAAATATTAACCGACATGTGGTACATAACCACTTGTA
``` a       F  D  P  K  Q  L  Q  M  F  I  I  G  C  T  P  C  I  G  E  H       -

```
    TGGGATAAGGCTCCTGCATGTGTTAATGATATTCAACAAGGTAGTTGCCCACCAATAGAA
181 ---------+---------+---------+---------+---------+---------+ 240
    ACCCTATTCCGAGGACGTACACAATTACTATAAGTTGTTCCATCAACGGGTGGTTATCTT
``` a       W  D  K  A  P  A  C  V  N  D  I  Q  Q  G  S  C  P  P  I  E       -

```
    TTAGTTAACACATACATACAGGGTGGAGATATGGCTGATATAGGATATGGCAATCTAAAT
241 ---------+---------+---------+---------+---------+---------+ 300
    AATCAATTGTGTATGTATGTCCCACCTCTATACCGACTATATCCTATACCGTTAGATTTA
``` a       L  V  N  T  Y  I  Q  G  G  D  M  A  D  I  G  Y  G  N  L  N       -

```
    TTTAAAGCTTTACAGCAAAATAGATCAGATGTTAGCTTGGATATTGTAGATGAAATATGC
301 ---------+---------+---------+---------+---------+---------+ 360
    AAATTTCGAAATGTCGTTTTATCTAGTCTACAATCGAACCTATAACATCTACTTTATACG
``` a       F  K  A  L  Q  Q  N  R  S  D  V  S  L  D  I  V  D  E  I  C       -

```
    AAATATCCTGACTTTTTACGAATGCAAAATGATGTATATGGCGATGCCTGTTTTTTTTAT
361 ---------+---------+---------+---------+---------+---------+ 420
    TTTATAGGACTGAAAAATGCTTACGTTTTACTACATATACCGCTACGGACAAAAAAAATA
``` a       K  Y  P  D  F  L  R  M  Q  N  D  V  Y  G  D  A  C  F  F  Y       -

```
    GCTCGACGGGAGCAATGTTATGCCAGGCACTTTTTTGTGCGTGGTGGCAAACCTGGTGAT
421 ---------+---------+---------+---------+---------+---------+ 480
    CGAGCTGCCCTCGTTACAATACGGTCCGTGAAAAAACACGCACCACCGTTTGGACCACTA
``` a       A  R  R  E  Q  C  Y  A  R  H  F  F  V  R  G  G  K  P  G  D       -

FIG. 4-B

```
      GATATACCTGGTGCCCAAATTGATGCAGGGTCACATAAAAATGAATATTACATACAGGCA
  481 ----------+----------+----------+----------+----------+----------+ 540
      CTATATGGACCACGGGTTTAACTACGTCCCAGTGTATTTTTACTTATAATGTATGTCCGT a      D  I  P  G  A  Q  I  D  A  G  S  H  K  N  E  Y  Y  I  Q  A    -

GCTTCAGACCAATCACAAAATAGTTTGGGGAATTCTATGTATTTCCCAACTATCAGTGGC
  541 ----------+----------+----------+----------+----------+----------+ 600
      CGAAGTCTGGTTAGTGTTTTATCAAACCCCTTAAGATACATAAAGGGTTGATAGTCACCG a      A  S  D  Q  S  Q  N  S  L  G  N  S  M  Y  F  P  T  I  S  G    -

TCATTAGTTTCAAGTGATGCTCAATTATTTAATAGGCCCTTCTGGCTACAGCGAGCACAA
  601 ----------+----------+----------+----------+----------+----------+ 660
      AGTAATCAAAGTTCACTACGAGTTAATAAATTATCCGGGAAGACCGATGTCGCTCGTGTT a      S  L  V  S  S  D  A  Q  L  F  N  R  P  F  W  L  Q  R  A  Q    -

GGCCAAAACAACGGGAT
  661 ----------+------- 677
      CCGGTTTTGTTGCCCTA
```

FIG. 5-A

```
    TCAAGGGGACAGCCATTGGGTGTAGGAACATCAGGTCATCCTTTATTTAACAAAGTCAGG
  1 ---------+---------+---------+---------+---------+---------+  60
    AGTTCCCCTGTCGGTAACCCACATCCTTGTAGTCCAGTAGGAAATAAATTGTTTCAGTCC a   S  R  G  Q  P  L  G  V  G  T  S  G  H  P  L  F  N  K  V  R   -

GATACTGAAAACTCAGGTAACTATCAAGCAGTTTCTCAGGATGACAGACAAAATACATCT
 61 ---------+---------+---------+---------+---------+---------+ 120
    CTATGACTTTTGAGTCCATTGATAGTTCGTCAAAGAGTCCTACTGTCTGTTTTATGTAGA a   D  T  E  N  S  G  N  Y  Q  A  V  S  Q  D  D  R  Q  N  T  S   -

TTTGATCCTAAACAAGTGCAAATGTTTGTCATTGGCTGTGTGCCGTGTATGGGTGAACAT
121 ---------+---------+---------+---------+---------+---------+ 180
    AAACTAGGATTTGTTCACGTTTACAAACAGTAACCGACACACGGCACATACCCACTTGTA a   F  D  P  K  Q  V  Q  M  F  V  I  G  C  V  P  C  M  G  E  H   -

TGGGACAAAGCTAAGGTTTGTGAATCAGAAGCAAATAATCAACAAGGCTTATGTCCACCC
181 ---------+---------+---------+---------+---------+---------+ 240
    ACCCTGTTTCGATTCCAAACACTTAGTCTTCGTTTATTAGTTGTTCCGAATACAGGTGGG a   W  D  K  A  K  V  C  E  S  E  A  N  N  Q  Q  G  L  C  P  P   -

ATAGAGTTAAAAAATTCAGTAATTGAAGATGGAGATATGTTTGATATAGGCTTTGGAAAT
241 ---------+---------+---------+---------+---------+---------+ 300
    TATCTCAATTTTTTAAGTCATTAACTTCTACCTCTATACAAACTATATCCGAAACCTTTA a   I  E  L  K  N  S  V  I  E  D  G  D  M  F  D  I  G  F  G  N   -

ATTAATAACAAAGCACTATCTTATAACAAGTCAGATGTTAGTTTAGATATAGTTAATGAA
301 ---------+---------+---------+---------+---------+---------+ 360
    TAATTATTGTTTCGTGATAGAATATTGTTCAGTCTACAATCAAATCTATATCAATTACTT a   I  N  N  K  A  L  S  Y  N  K  S  D  V  S  L  D  I  V  N  E   -

GTGTGCAAATATCCAGACTTTTTAACCATGGCTAATGATGTGTATGGAGATGCTTGTTTT
361 ---------+---------+---------+---------+---------+---------+ 420
    CACACGTTTATAGGTCTGAAAAATTGGTACCGATTACTACACATACCTCTACGAACAAAA a   V  C  K  Y  P  D  F  L  T  M  A  N  D  V  Y  G  D  A  C  F   -

TTCTTTGCTAGACGAGAACAATGTTATGCCAGACATTATTTTGTTAGGGGAGGCAATGTT
421 ---------+---------+---------+---------+---------+---------+ 480
    AAGAAACGATCTGCTCTTGTTACAATACGGTCTGTAATAAAACAATCCCCTCCGTTACAA a   F  F  A  R  R  E  Q  C  Y  A  R  H  Y  F  V  R  G  G  N  V   -
```

FIG. 5-B

```
         GGCGATGCAATCCCTGATGGAGCAGTACAACAGGATCACAACTATTATTTACCTGCACAA
     481 ---------+---------+---------+---------+---------+---------+ 540
         CCGCTACGTTAGGGACTACCTCGTCATGTTGTCCTAGTGTTGATAATAAATGGACGTGTT a        G   D   A   I   P   D   G   A   V   Q   Q   D   H   N   Y   Y   L   P   A   Q    -

AATGCACAGCAACAACACACCTTGGGAAATTCTATATATTATCCAACTGTTAGTGGGTCT
     541 ---------+---------+---------+---------+---------+---------+ 600
         TTACGTGTCGTTGTTGTGTGGAACCCTTTAAGATATATAATAGGTTGACAATCACCCAGA a        N   A   Q   Q   H   T   L   G   N   S   I   Y   Y   P   T   V   S   G   S    -

CTTGTAACATCTGATGCTCAGTTATTTAATAGACCATTTTGGTTACAACGTGCTCAAGGA
     601 ---------+---------+---------+---------+---------+---------+ 660
         GAACATTGTAGACTACGAGTCAATAAATTATCTGGTAAAACCAATGTTGCACGAGTTCCT a        L   V   T   S   D   A   Q   L   F   N   R   P   F   W   L   Q   R   A   Q   G    -

CAAAACAACGGTAT
     661 ---------+---- 674
         GTTTTGTTGCCATA
```

FIG. 6-A

```
    GGTAGTGGGCAACCATTAGGTGTAGGCACCACAGGACATCCACTGTTTAATAAACTTAGA
  1 ----------+----------+----------+----------+----------+----------+  60
    CCATCACCCGTTGGTAATCCACATCCGTGGTGTCCTGTAGGTGACAAATTATTTGAATCT
``` a     G   S   G   Q   P   L   G   V   G   T   T   G   H   P   L   F   N   K   L   R     -

```
     GATTCAGAAAATTCTGCAGAACGTCTGGAAGGAACAAGTGATGATAGGAGGAATATATCA
  61 ----------+----------+----------+----------+----------+----------+  120
     CTAAGTCTTTTAAGACGTCTTGCAGACCTTCCTTGTTCACTACTATCCTCCTTATATAGT
``` a     D   S   E   N   S   A   E   R   L   E   G   T   S   D   D   R   R   N   I   S     -

```
      TTTGATCCTAAGCAAGTGCAAATGTTTGTGATAGGCTGCACCCCCTGTTTAGGGGAGTAT
  121 ----------+----------+----------+----------+----------+----------+  180
      AAACTAGGATTCGTTCACGTTTACAAACACTATCCGACGTGGGGGACAAATCCCCTCATA
``` a     F   D   P   K   Q   V   Q   M   F   V   I   G   C   T   P   C   L   G   E   Y     -

```
      TGGGATACAGCTCCAGTATGTAAAGATGCAGGAAGTCAATTAGGCCTTTGCCCTCCATTA
  181 ----------+----------+----------+----------+----------+----------+  240
      ACCCTATGTCGAGGTCATACATTTCTACGTCCTTCAGTTAATCCGGAAACGGGAGGTAAT
``` a     W   D   T   A   P   V   C   K   D   A   G   S   Q   L   G   L   C   P   P   L     -

```
      GAATTAAAAAACAGTGTTATAGAAGATGGCGATATGTTTGATATAGGATTTGGCAATATT
  241 ----------+----------+----------+----------+----------+----------+  300
      CTTAATTTTTTGTCACAATATCTTCTACCGCTATACAAACTATATCCTAAACCGTTATAA
``` a     E   L   K   N   S   V   I   E   D   G   D   M   F   D   I   G   F   G   N   I     -

```
      AACAACAAAACATTAAGTTTTAATAAGTCAGATGTTAGTGTGGACATTGTTAATGAAATT
  301 ----------+----------+----------+----------+----------+----------+  360
      TTGTTGTTTTGTAATTCAAAATTATTCAGTCTACAATCACACCTGTAACAATTACTTTAA
``` a     N   N   K   T   L   S   F   N   K   S   D   V   S   V   D   I   V   N   E   I     -

```
      TGTAAATATCCTGATTTTTTAACTATGTCCAATGATGTTTATGGAGACTCTTGCTTTTTC
  361 ----------+----------+----------+----------+----------+----------+  420
      ACATTTATAGGACTAAAAAATTGATACAGGTTACTACAAATACCTCTGAGAACGAAAAAG
``` a     C   K   Y   P   D   F   L   T   M   S   N   D   V   Y   G   D   S   C   F   F     -

```
      TTTGCTCGCAGAGAGCGATGTTATGCAAGGCATTATTTTGTACGCGGAGGGGCAGTGGGT
  421 ----------+----------+----------+----------+----------+----------+  480
      AAACGAGCGTCTCTCGCTACAATACGTTCCGTAATAAAACATGCGCCTCCCCGTCACCCA
``` a     F   A   R   R   E   R   C   Y   A   R   H   Y   F   V   R   G   G   A   V   G     -

FIG. 6-B

```
    GATTTAATACCAGATGCTACAGTTAATCAGGACCATAAATATTACTTACCAGCAAATCCA
481 ----------+----------+----------+----------+----------+----------+ 540
    CTAAATTATGGTCTACGATGTCAATTAGTCCTGGTATTTATAATGAATGGTCGTTTAGGT
``` a      D  L  I  P  D  A  T  V  N  Q  D  H  K  Y  Y  L  P  A  N  P    -

```
    CCTGCCACATTGGAAAACTCTACATACTTTCCGACTGCTAGTGGCTCCTTAGTGACATCT
541 ----------+----------+----------+----------+----------+----------+ 600
    GGACGGTGTAACCTTTTGAGATGTATGAAAGGCTGACGATCACCGAGGAATCACTGTAGA
``` a      P  A  T  L  E  N  S  T  Y  F  P  T  A  S  G  S  L  V  T  S    -

```
    GATGCACAATTATTTAATAGGCCCTTTTGGTTAAAACGTGCACAAGGTCATAATAATGGT
601 ----------+----------+----------+----------+----------+----------+ 660
    CTACGTGTTAATAAATTATCCGGGAAAACCAATTTTGCACGTGTTCCAGTATTATTACCA
``` a      D  A  Q  L  F  N  R  P  F  W  L  K  R  A  Q  G  H  N  N  G    -

```
    GGTAGGGGGCAACCATTTGGGGTAGGCACTACAGGTCATCCATTATTTAACAAATTACGT
  1 ------------+---------+---------+---------+---------+---------+ 60
    CCATCCCCCGTTGGTAAACCCCATCCGTGATGTCCAGTAGGTAATAAATTGTTTAATGCA a    G  R  G  Q  P  F  G  V  G  T  T  G  H  P  L  F  N  K  L  R  -

GATGCAGAAAATTCCAGCGAACGTCAGGGAGATACTGCTGCAGATGACAGAATGAATATA
 61 ------------+---------+---------+---------+---------+---------+ 120
    CTACGTCTTTTAAGGTCGCTTGCAGTCCCTCTATGACGACGTCTACTGTCTTACTTATAT a    D  A  E  N  S  S  E  R  Q  G  D  T  A  A  D  D  R  M  N  I  -

TCTTTTGATCCTAAGCAGGTACAAATGTTCATAATAGGTTGCACACCGTGTTTAGGTGAA
121 ------------+---------+---------+---------+---------+---------+ 180
    AGAAAACTAGGATTCGTCCATGTTTACAAGTATTATCCAACGTGTGGCACAAATCCACTT a    S  F  D  P  K  Q  V  Q  M  F  I  I  G  C  T  P  C  L  G  E  -

TATTGGGATCAAGCGCCTGTATGTAAAGATGCAGGTAACCAAATGGGCTTATGTCCTCCT
181 ------------+---------+---------+---------+---------+---------+ 240
    ATAACCCTAGTTCGCGGACATACATTTCTACGTCCATTGGTTTACCCGAATACAGGAGGA a    Y  W  D  Q  A  P  V  C  K  D  A  G  N  Q  M  G  L  C  P  P  -

CTTGAACTAAAGAATAGTGTCATAGAAGATGGAGATATGTTTGATATAGGCTTTGGTAAC
241 ------------+---------+---------+---------+---------+---------+ 300
    GAACTTGATTTCTTATCACAGTATCTTCTACCTCTATACAAACTATATCCGAAACCATTG a    L  E  L  K  N  S  V  I  E  D  G  D  M  F  D  I  G  F  G  N  -

ATTAATAATAAGACACTGTCATTCAATAGATCAGATGTTAGTTTAGATATTGTAAATGAA
301 ------------+---------+---------+---------+---------+---------+ 360
    TAATTATTATTCTGTGACAGTAAGTTATCTAGTCTACAATCAAATCTATAACATTTACTT a    I  N  N  K  T  L  S  F  N  R  S  D  V  S  L  D  I  V  N  E  -

ATATGCAAATATCCAGATTTTTTAACAATGTCCAATGATGTTTATGGTGACTCCTGTTTT
361 ------------+---------+---------+---------+---------+---------+ 420
    TATACGTTTATAGGTCTAAAAAATTGTTACAGGTTACTACAAATACCACTGAGGACAAAA a    I  C  K  Y  P  D  F  L  T  M  S  N  D  V  Y  G  D  S  C  F  -

TTTTGTGCTCGAAGAGAGCAATGTTATGCTAGACATTATTTTGTACGAGGCGGTGTTGTT
421 ------------+---------+---------+---------+---------+---------+ 480
    AAAACACGAGCTTCTCTCGTTACAATACGATCTGTAATAAAACATGCTCCGCCACAACAA a    F  C  A  R  R  E  Q  C  Y  A  R  H  Y  F  V  R  G  G  V  V  -
```

FIG. 7-B

```
    GGAGATTCTATACCAGACGGTGCAGTCCAGCAGAGTAACAAATATTATTTAGCTTCAGCT
481 ---------+---------+---------+---------+---------+---------+ 540
    CCTCTAAGATATGGTCTGCCACGTCAGGTCGTCTCATTGTTTATAATAAATCGAAGTCGA a    G  D  S  I  P  D  G  A  V  Q  Q  S  N  K  Y  Y  L  A  S  A   -

CAAAATAATAGCTTGGAAAATTCTACCTATTTCCCAACTGTAAGTGGTTCTTTAGTGACT
541 ---------+---------+---------+---------+---------+---------+ 600
    GTTTTATTATCGAACCTTTTAAGATGGATAAAGGGTTGACATTCACCAAGAAATCACTGA a    Q  N  N  S  L  E  N  S  T  Y  F  P  T  V  S  G  S  L  V  T   -

TCTGATGCTCAGCTATTTAACAGACCCTTTTGGTTAAAGCGTGCTCAAGGGCATAATAAT
601 ---------+---------+---------+---------+---------+---------+ 660
    AGACTACGAGTCGATAAATTGTCTGGGAAAACCAATTTCGCACGAGTTCCCGTATTATTA a    S  D  A  Q  L  F  N  R  P  F  W  L  K  R  A  Q  G  H  N  N   -

GGAAT
661 ----- 665
    CCTTA
```

FIG. 8-A

```
       GGAAGAGGTCTCCATTTGGGTGTAGGTACAGCAGGCCATCCACTATTCAATAAAGTTAGA
     1 ------------+----------+----------+----------+----------+    60
       CCTTCTCCAGAGGTAAACCCACATCCATGTCGTCCGGTAGGTGATAAGTTATTTCAATCT a      G  R  G  L  H  L  G  V  G  T  A  G  H  P  L  F  N  K  V  R    -

GATACAGAAAATAATAGTGGCTATCAAGATACGTCTACGGATGACAGACAAAATACATCA
    61 ------------+----------+----------+----------+----------+   120
       CTATGTCTTTTATTATCACCGATAGTTCTATGCAGATGCCTACTGTCTGTTTTATGTAGT a      D  T  E  N  N  S  G  Y  Q  D  T  S  T  D  D  R  Q  N  T  S    -

TTTGATCCAAAACAAGTTCAAATGTTTGTAGTAGGATGTGCTCCTTGTTTGGGAGAACAT
   121 ------------+----------+----------+----------+----------+   180
       AAACTAGGTTTTGTTCAAGTTTACAAACATCATCCTACACGAGGAACAAACCCTCTTGTA a      F  D  P  K  Q  V  Q  M  F  V  V  G  C  A  P  C  L  G  E  H    -

TGGGATAAAGCTCCTGTCTGTGACTCAGATAAAAATAACCAGGCTGGAAAATGCCCTCCA
   181 ------------+----------+----------+----------+----------+   240
       ACCCTATTTCGAGGACAGACACTGAGTCTATTTTTATTGGTCCGACCTTTTACGGGAGGT a      W  D  K  A  P  V  C  D  S  D  K  N  N  Q  A  G  K  C  P  P    -

TTAGAACTGAGAAACACAGTAATAGAAGATGGAGATATGATTGATATAGGCTTTGGCAAT
   241 ------------+----------+----------+----------+----------+   300
       AATCTTGACTCTTTGTGTCATTATCTTCTACCTCTATACTAACTATATCCGAAACCGTTA a      L  E  L  R  N  T  V  I  E  D  G  D  M  I  D  I  G  F  G  N    -

ATAAACAACAAGGTTTTATCAGTTACTAAGTCAGATGTTAGTCTGGATATAGTTAATGAA
   301 ------------+----------+----------+----------+----------+   360
       TATTTGTTGTTCCAAAATAGTCAATGATTCAGTCTACAATCAGACCTATATCAATTACTT a      I  N  N  K  V  L  S  V  T  K  S  D  V  S  L  D  I  V  N  E    -

ACTTGTAAGTATCCAGATTTTTTAACTATGGCCAATGATGTATATGGTGACTCTTGTTTT
   361 ------------+----------+----------+----------+----------+   420
       TGAACATTCATAGGTCTAAAAAATTGATACCGGTTACTACATATACCACTGAGAACAAAA a      T  C  K  Y  P  D  F  L  T  M  A  N  D  V  Y  G  D  S  C  F    -

TTCTTTGCAAGGAGAGAACAGTGTTATGCTAGACATTATTATGTTAGGGGAGGTGTAGTA
   421 ------------+----------+----------+----------+----------+   480
       AAGAAACGTTCCTCTCTTGTCACAATACGATCTGTAATAATACAATCCCCTCCACATCAT a      F  F  A  R  R  E  Q  C  Y  A  R  H  Y  Y  V  R  G  G  V  V    -
```

FIG. 8-B

```
        GGTGATGCTATTCCTGATGAAGCTGTGAATCAAGATAAAAACTTTGTGTTACCTGCACAA
    481 ---------+---------+---------+---------+---------+---------+ 540
        CCACTACGATAAGGACTACTTCGACACTTAGTTCTATTTTTGAAACACAATGGACGTGTT a       G  D  A  I  P  D  E  A  V  N  Q  D  K  N  F  V  L  P  A  Q    -

GGCACTCAGCAACAAAAGGATATAGCTAGTTCTATATATTTTCCAACTGTTAGTGGTTCC
    541 ---------+---------+---------+---------+---------+---------+ 600
        CCGTGAGTCGTTGTTTTCCTATATCGATCAAGATATATAAAAGGTTGACAATCACCAAGG a       G  T  Q  Q  Q  K  D  I  A  S  S  I  Y  F  P  T  V  S  G  S    -

TTAGTAACTTCTGATGCTCAATTATTTAACAGACCATTTTGGTTACGCAGAGCACAAGGG
    601 ---------+---------+---------+---------+---------+---------+ 660
        AATCATTGAAGACTACGAGTTAATAAATTGTCTGGTAAAACCAATGCGTCTCGTGTTCCC a       L  V  T  S  D  A  Q  L  F  N  R  P  F  W  L  R  R  A  Q  G    -

CAAAATAACGGGAT
    661 ---------+---- 674
        GTTTTATTGCCCTA
```

FIG. 9-A

```
    GGGAGAGGACAGCCATTAGGCGTTGGTACCAGTGGACATCCACTGTTTAACAAAGTTAAT
  1 ------------+---------+---------+---------+---------+---------+  60
    CCCTCTCCTGTCGGTAATCCGCAACCATGGTCACCTGTAGGTGACAAATTGTTTCAATTA a    G  R  G  Q  P  L  G  V  G  T  S  G  H  P  L  F  N  K  V  N   -

GATGCCGAAAATCCCTTAGCTTACAGGGCACAGGCCTTTTCTACTGATGATAGGCAAAAC
 61 ---------+---------+---------+---------+---------+---------+  120
    CTACGGCTTTTAGGGAATCGAATGTCCCGTGTCCGGAAAAGATGACTACTATCCGTTTTG a    D  A  E  N  P  L  A  Y  R  A  Q  A  F  S  T  D  D  R  Q  N   -

ACATCCTTTGATCCTAAACAAATACAAATGTTTATAATAGGTTGTGCACCCTGTATTGGA
121 ---------+---------+---------+---------+---------+---------+  180
    TGTAGGAAACTAGGATTTGTTTATGTTTACAAATATTATCCAACACGTGGGACATAACCT a    T  S  F  D  P  K  Q  I  Q  M  F  I  I  G  C  A  P  C  I  G   -

GAGCATTGGGATGTAGGTGAACGTTGTGCAGGAGCCAATAATGAAAATGGTCGATGCCCC
181 ---------+---------+---------+---------+---------+---------+  240
    CTCGTAACCCTACATCCACTTGCAACACGTCCTCGGTTATTACTTTTACCAGCTACGGGG a    E  H  W  D  V  G  E  R  C  A  G  A  N  N  E  N  G  R  C  P   -

CCTATTAAATTGGTAAATTCAGTCATCCAAGATGGAGATATGGCAGATATTGGTTATGGA
241 ---------+---------+---------+---------+---------+---------+  300
    GGATAATTTAACCATTTAAGTCAGTAGGTTCTACCTCTATACCGTCTATAACCAATACCT a    P  I  K  L  V  N  S  V  I  Q  D  G  D  M  A  D  I  G  Y  G   -

AACCTAAATTTCCGTACCTTACAGGAAAACAGATCTGATGTAAGTTTAGATATAGTGAAT
301 ---------+---------+---------+---------+---------+---------+  360
    TTGGATTTAAAGGCATGGAATGTCCTTTTGTCTAGACTACATTCAAATCTATATCACTTA a    N  L  N  F  R  T  L  Q  E  N  R  S  D  V  S  L  D  I  V  N   -

GAAACCTGTAAATATCCAGACTTTTTAAAGATGCAGAATGATATATATGGCGATTCTTGC
361 ---------+---------+---------+---------+---------+---------+  420
    CTTTGGACATTTATAGGTCTGAAAAATTTCTACGTCTTACTATATATACCGCTAAGAACG a    E  T  C  K  Y  P  D  F  L  K  M  Q  N  D  I  Y  G  D  S  C   -

TTTTTCTTTGCTCGCCGGGAGCAATGTTATGCAAGACATTTTTTTGTTCGTGGGGGTAAG
421 ---------+---------+---------+---------+---------+---------+  480
    AAAAAGAAACGAGCGGCCCTCGTTACAATACGTTCTGTAAAAAACAAGCACCCCCATTC a    F  F  F  A  R  R  E  Q  C  Y  A  R  H  F  F  V  R  G  G  K   -
```

FIG. 9-B

```
      GCGGGGGATGACATTCCTGGTGCGCAAATCGATGCAGGTACATATAAAAATGATTTTTAC
  481 ---------+---------+---------+---------+---------+---------+ 540
      CGCCCCCTACTGTAAGGACCACGCGTTTAGCTACGTCCATGTATATTTTTACTAAAAATG a     A  G  D  D  I  P  G  A  Q  I  D  A  G  T  Y  K  N  D  F  Y   -

ATACCTGGAGCGTCAGGTCAGACACAAAAGAATATAGGTAACTCGATGTATTTCCCAACA
  541 ---------+---------+---------+---------+---------+---------+ 600
      TATGGACCTCGCAGTCCAGTCTGTGTTTTCTTATATCCATTGAGCTACATAAAGGGTTGT a     I  P  G  A  S  G  Q  T  Q  K  N  I  G  N  S  M  Y  F  P  T   -

GTAAGTGGCTCATTGGTGTCTAGTGATGCTCAATTGTTTAATAGGCCCTTCTGGCTCCAA
  601 ---------+---------+---------+---------+---------+---------+ 660
      CATTCACCGAGTAACCACAGATCACTACGAGTTAACAAATTATCCGGGAAGACCGAGGTT a     V  S  G  S  L  V  S  S  D  A  Q  L  F  N  R  P  F  W  L  Q   -

CGGGCGCAGGGGCAAAACAACGGAAT
  661 ---------+---------+------ 686
      GCCCGCGTCCCCGTTTTGTTGCCTTA
```

6,025,163

DNA CODING FOR A PEPTIDE OF A PAPILLOMA VIRUS MAIN CAPSIDE PROTEIN AND USE THEREOF this is a rule 371 application based on priority date of PCT/EP95/01697 filed May 04, 1995.

I. FIELD OF THE INVENTION

The present invention relates to a DNA encoding a peptide of a papilloma virus major capsid protein. Furthermore, this invention concerns a papilloma virus genome containing such a DNA. In addition, this invention relates to proteins encoded by the papilloma virus genome and to virus-like particles as well as antibodies directed thereagainst and the use thereof in diagnosis, treatment and vaccination.

II. BACKGROUND OF THE INVENTION

It is well known that papilloma viruses infect the epithelial tissue of humans and animals. Human papilloma viruses (referred to as HP viruses below) are found in benign, e.g., warts, condylomata in the genital region, and malign, e.g., carcinomas of the skin and uterus, epithelial neoplasms. Zur Hausen, 1989, *Cancer Research* 49:4677–4681. HP viruses are also considered for the development of malign tumors of the respiratory tract. Zur Hausen, 1976, *Cancer Research* 36:530. In addition, HP viruses are considered at least co-responsible for the development of squamous carcinomas of the lungs. Syrjänen, 1980, *Lung* 158:131–142.

Papilloma viruses have an icosahedral capsid without coat, which includes a circular, double-stranded DNA molecule of about 7,900 bp. The capsid comprises a major capsid protein (L1) and a minor capsid protein (L2). Both proteins, coexpressed or L1 expressed alone, result in vitro to the development of virus-like particles. Kirnbauer et al., 1993, *Journal of Virology* 67:6929–6936.

Papilloma viruses cannot be proliferated in monolayer cell culture. Therefore, their characterization is extremely difficult, the detection of papilloma viruses already creating considerable problems. This applies particularly to papilloma viruses in carcinomas of the skin. A reliable detection thereof and thus well-calculated steps thereagainst have not been possible by now.

Therefore, it is the object of the present invention to provide an agent serving for detecting papilloma viruses, particularly in carcinomas of the skin. Furthermore, an agent is to be provided which serves for taking therapeutic steps against these papilloma viruses.

According to the inventions this is achieved by the provision of the subject matters in the claims.

III. SUMMARY OF THE INVENTION

The present invention is directed to a DNA encoding a peptide of a papilloma virus major capsid protein.

The present invention is also directed to a papilloma virus genome containing such a DNA.

The present invention is further directed to proteins encoded by the papilloma virus genome and to virus-like articles as well as antibodies directed thereagainst and the use thereof in diagnosis, treatment and vaccination.

IV. BRIEF DESCRIPTION OF THE DRAWINGS

FIG. 1 shows the base sequence and the amino acid sequence, derived therefrom, of a DNA encoding a peptide of L1 of a papilloma virus (SEQ ID NO:1). This DNA was deposited as plasmid VS93-1 with the DSM (German Collection of Microorganisms and Cell Cultures) under DSM 9133 on Apr. 12, 1994.

FIG. 2 shows the base sequence and the amino acid sequence, derived therefrom, of an DNA encoding a peptide of L1 of a papilloma virus (SEQ ID NO:2). This DNA was deposited as plasmid CR148-59 with the DSM under DSM 9134 on Apr. 12, 1994.

FIG. 3 shows the base sequence and the amino acid sequence, derived therefrom, of an DNA encoding a peptide of L1 of a papilloma virus (SEQ ID NO:3). This DNA was deposited as plasmid VS40-7 with the DSM under DSM 9135 on Apr. 12, 1994.

FIG. 4 shows the base sequence and the amino acid sequence, derived therefrom, of an DNA encoding a peptide of L1 of a papilloma virus (SEQ ID NO:4). This DNA was deposited as plasmid VS20-4 with the DSM under DSM 9136 on Apr. 12, 1994.

FIG. 5 shows the base sequence and the amino acid sequence, derived therefrom, of an DNA encoding a peptide of L1 of a papilloma virus (SEQ ID NO:5). This DNA was deposited as plasmid VS102-4 with the DSM under DSM 9137 on Apr. 12, 1994.

FIG. 6 shows the base sequence and the amino acid sequence, derived therefrom, of an DNA encoding a peptide of L1 of a papilloma virus (SEQ ID NO:6). This DNA was deposited as plasmid VS73-1 with the DSM under DSM 9138 on Apr. 12, 1994.

FIG. 7 shows the base sequence and the amino acid sequence, derived therefrom, of an DNA encoding a peptide of L1 of a papilloma virus (SEQ ID NO:7). This DNA was deposited as plasmid VS42-1 with the DSM under DSM 9139 on Apr. 12, 1994.

FIG. 8 shows the base sequence and the amino acid sequence, derived therefrom, of an DNA encoding a peptide of L1 of a papilloma virus (SEQ ID NO:8). This DNA was deposited as plasmid VS92-1 with the DSM under DSM 9140 on Apr. 12, 1994.

FIG. 9 shows the base sequence and the amino acid sequence, derived therefrom, of an DNA encoding a peptide of L1 of a papilloma virus (SEQ ID NO:9). This DNA was deposited as plasmid VS75-3 with the DSM under DSM 9141 on Apr. 12, 1994.

V. DETAILED DESCRIPTION OF THE INVENTION

Figure 10:
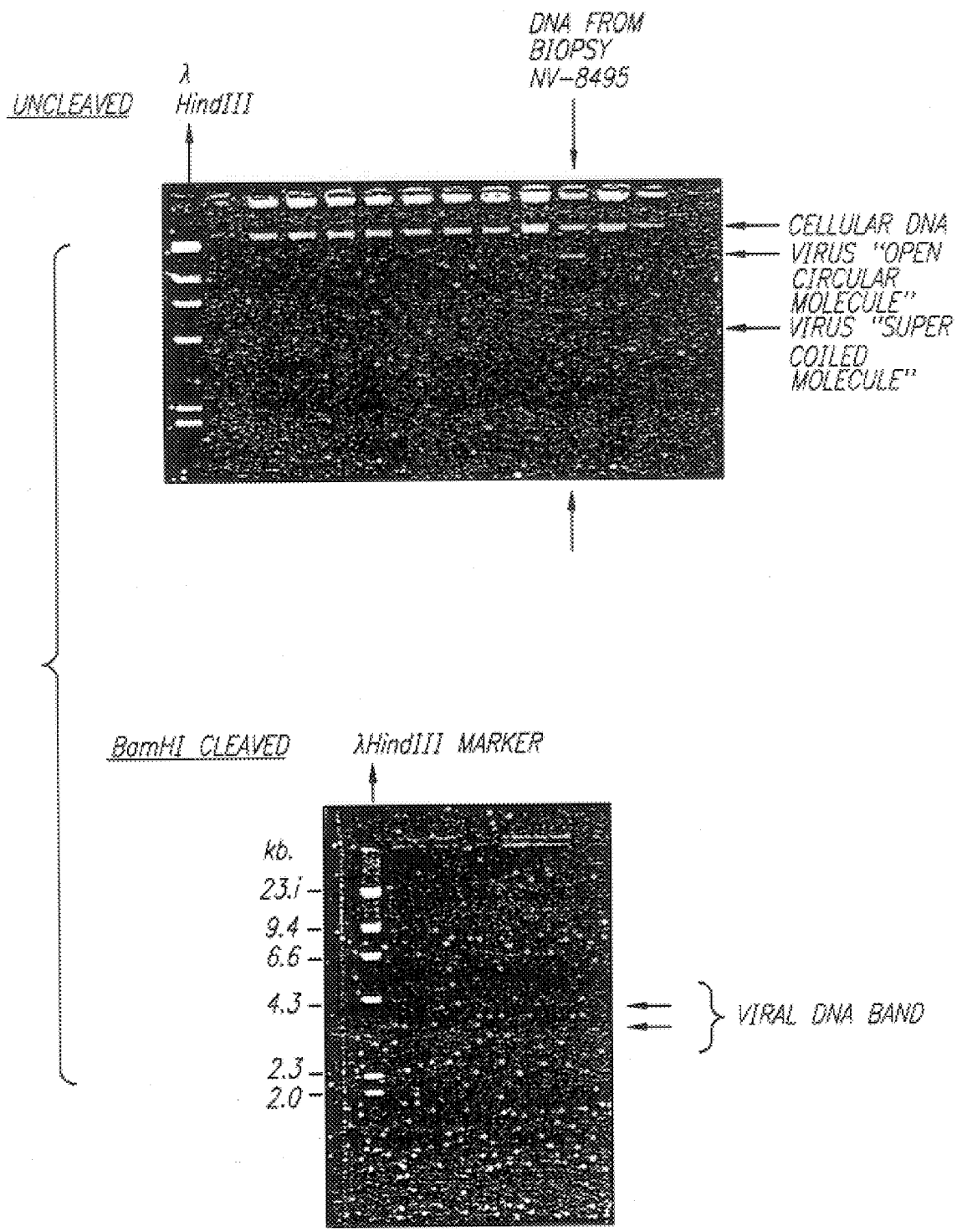

According to its objective, the subject matter of this invention relates to a DNA encoding a peptide of a papilloma virus major capsid protein (L1), the peptide comprising at least a portion of the amino acid sequence of the amino acid sequence of FIG. 1, FIG. 2, FIG. 3, FIG. 4, FIG. 5, FIG. 6, FIG. 7, FIG. 8, or FIG. 9.

The expression "at least a portion of the amino acid sequence" of the individual figures may also include a variation of one or more amino acids.

Another subject matter of the invention deals with a DNA encoding a peptide of a papilloma virus major capsid protein, the DNA comprising at least a portion of the vase sequence or the base sequence of FIG. 1, FIG. 2, FIG. 3, FIG. 4, FIG. 5, FIG. 6, FIG. 7, FIG. 8, or FIG. 9.

The expression "at least a portion of the base sequence" refers to the fact that the base sequence of the individual figures may also include a variation of one or more base pairs.

The above DNA as described in the drawings has the following sequence homology with known papilloma viruses:

DNA of FIG. 1: 82.7% with HP virus 29
DNA of FIG. 2: 75% with HP virus 49
DNA of FIG. 3: 78.5% with HP virus 49
DNA of FIG. 4: 75.6% with HP virus 25
DNA of FIG. 5: 79% with HP virus 17
DNA of FIG. 6: 73.6% with HP virus 17
DNA of FIG. 7: 73.1% with HP virus 15
DNA of FIG. 8: 82.8% with HP virus 15
DNA of FIG. 9: 75.7% with HP virus 12.

According to the invention the above DNA may exist in a vector and an expression vector, respectively. A person skilled in the art is familiar with examples thereof. In the case of an expression vector for E. coli, these are e.g., pGEMEX, pUC derivatives and pGEX-2T. For the expression in yeast, e.g., pY100 and Ycpad1 have to be mentioned, while for the expression in animal cells, e.g., pKCR, pEF-BOS, cDM8 and pCEV4 have been indicated. The person skilled in the art knows suitable cells to express the above DNA present in an expression vector. Examples of such cells comprise the E. coli strains HB101, DH1, x1776, JM101 and JM109 the yeast strain Saccharomyces cerevisiae and the animal cells L, 3T3, FM3A, CHO, COS, Vero and Hela. The person skilled in the art knows in which way the above DNA has to be inserted in an expression vector. He is also familiar with the fact that the above DNA can be inserted in combination with a DNA encoding another protein and peptide, respectively, so that the above DNA can be expressed in the form of a fused protein.

Another subject matter of the invention relates to a papilloma virus genome which comprise the above DNA. The expression "papilloma virus genome" also comprises an incomplete genome, i.e. fragments of a papilloma virus genome, which comprise the above DNA. This may be, e.g., a DNA encoding L1or a portion thereof.

For providing the above papilloma virus genome it is possible to use a method which comprises the following steps:

(a) isolating the total DNA from a Biopsy of epithelial neoplasm, (b) hybridizing the total DNA of (a) with the above DNA thereby detecting a papilloma virus genome included in the total DNA of (a), and (c) cloning the total DNA of (a), including the papilloma virus genome, in a vector and optionally subcloning the resulting clone, all steps originating from conventional DNA recombination technique.

As regards the isolation, hybridization and cloning of cell DNA, reference is made to Sambrook et al., Molecular Cloning, A Laboratory Manual, second edition, Cold Spring Harbor Laboratory, 1989, by way of supplement.

The expression "epithelial neoplasm" comprises any neoplasms of the epithelial tissue in humans and animals. Examples of such neoplasms are warts, condylomata in the genital region and carcinomas of the skin. The latter are used preferable here to isolate the above papilloma virus genome.

The expression "vector" comprises any vectors suitable for cloning DNA which is chromosomal and extrachromosomal, respectively. Examples of such vectors are cosmids such as pWE15 and Super Cos1, and phages such as λ-phages, e.g., λZAP expression vector, λZAPII vector and λgt10 vector. λ-phages are preferred here. The above vectors are known and obtainable from the Stratagene company.

Papilloma virus genomes according to the invention may be integrated in chromosomal DNA or present in extrachromosomal form. The person skilled in the art is familiar with methods of clarifying this. He is also familiar with methods of finding out the optimum restriction enzymes for cloning the papilloma virus genomes. He will orient himself by genomes of known papilloma viruses. In particular, the person skilled in the art will observe the above-mentioned HP viruses correspondingly.

The provision of a papilloma virus genome referred to as VS93-1-G is described by way of example. For this purpose, the total DNA is isolated from a biopsy of a squamousepithelial carcinoma, cleaved by BamHI and separated electrophoretically in an agarose gel. Then, the agarose gel is subjected to a blotting method whereby the DAN is transferred to a nitrocellulose membrane. It is used in a hybridization method in which the DNA of FIG. 1 is employed, optionally in combination with a DNA of HP virus 29, as labeled sample. Hybridization with the papilloma virus DNA existing in the total DNA is obtained.

Furthermore, the above total DNA cleaved by BamHI is cloned in a λ-phage. The corresponding clones, i.e. the clones containing the papilloma virus DNA, are identified by hybridization with the DNA of FIG. 1, optionally in combination with a DNA of HP virus 29. The insert of these clones is then subjected to another cloning in a plasmid vector so as to obtain clone which contains the papilloma virus genome VS93-1-G. The genome is confirmed by sequencing.

Further papilloma virus genomes are provided in analogous manner. Corresponding to the DNAs used for their provision, they are referred to as: CR 148–59-G, VS40-7-G, VS20-4-G, VS102-4-G, VS73-1-G, VS42-1-G, VS-92-1-G and VS75-3-G, respectively.

Another subject matter of the invention relates to a protein which is encoded by the above papilloma virus genome. Such a protein is, e.g., a major capsid protein (L1) or a minor capsid protein (L2). An above protein is produced as usual. The production of L1 and L2, respectively, of the papilloma virus genome VS93-1-G is described by way of example. For this purpose, the HP virus 29 related to the DNA of FIG. 1 is used. The complete sequence thereof and the position of individual DNA regions encoding proteins are known. These DANs are identified on the papilloma virus genome VS93-1-G are parallel restriction cleavages of both genomes and subsequent hybridization with various fragments relating to the DNA encoding L1 and L2, respectively. They are confirmed by sequence. The DNA encoding L1 is referred to as VS93-1-G-L1-DNA and the DNA encoding L2 is referred to as VS93-1-G-L2-DNA.

Furthermore, the DNA encoding L1 and L2, respectively, is inserted in an expression vector. Examples thereof for E. coli, yeast and animal cells are mentioned above. In this connection, reference it made to the vector pGEX-2T as regards the expression in E. coli by way of supplement. Kirnbauer et al., supra. After inserting the VS93-1-G-L1-DNA and VS93-1-g-L2-DNA, there is obtained pGEX-2T-VS93-1-G-L1 and pGEX-2T-VS93-1-G-L2, respectively. After the transformation of E. coli, these expression vectors express a glutathione S-transferase-L1-fused protein and glutathione S-transferase-L2-fused protein, respectively. These proteins are purified as usual.

For another expression of the above DNA encoding L1 and L2, respectively, there is mentioned the bacculovirus system and vaccinia virus system, respectively. Expression vectors usable for this purpose are, e.g., pEV mod. and pSynwtV1 for the bacculovirus system. Kirnbauer et al., supra. For the vaccinia virus system, particularly vectors including the vaccinia virus "early" (p7.5k) and "late" (Psynth, p11K) promoters are to be mention. Hagensee et al., 1993, *Journal of Virology*, 67:315–322. The bacculovirus system is preferred here. Having inserted the above DNA encoding L1 and L2, respectively, in pEV mod., there is obtained pEVmod.-VS93-1-G-L1 and pEVmod.-VS93-1-G-L2, respectively.

The former expression vector alone or both expression vectors together lead to the formation of virus-like particles after the infection of SF-9 insect cells. In the former case, such a particle comprises an L1 protein, whereas in the latter case it contains L2 protein in addition to an L1 protein.

A virus-like particle of the latter case is also obtained in that the above SV93-1-G-L1 -DNA and VS93-1-G-L2-DNA are together inserted in the expression vector pSynwtVI and the resulting pSynwtVI VS93-1-G-L1/L2 is used for infecting SF-9 insect cells. The above virus-like particles are purified as usual. They also represent a subject matter of this invention.

Another subject matter of the invention concerns an antibody directed against an above-mentioned protein and virus-like particle, respectively. Such an antibody is produced as usual. It is described by way of example for the production of an antibody which is directed against a virus-like particle comprising L1 of VS993-1-G. for this purpose, the virus-like particle is injected subcutaneously into BALB/c mice. This injection is repeated at intervals of 3 weeks each. About 2 weeks after the last injection, the serum containing the antibody is isolated and tested as usual.

In a preferred embodiment, the antibody is a monoclonal antibody. for the production thereof, splenocites are taken from the mice after the above fourth injection and they are fused with myeloma ells as usual. Further cloning is also carried out according to known methods.

The present invention renders possible to detect papilloma viruses, particularly in carcinomas of the skin. For this purpose, the DNA according to the invention can be used as such or included in another DNA. The latter may also be a papilloma virus genome or a portion thereof.

Furthermore, the present invention renders possible to provide formerly unknown viruses. They are found particularly in carcinomas of the skin. In addition, this invention supplies proteins and virus-like particles which originate from these papilloma viruses. Besides, antibodies are provided which are directed against these proteins and particles, respectively.

Thus, the present invention renders possible to take diagnostic and therapeutic steps in the case of papilloma virus diseases. Moreover, it furnishes the possibility of preparing a vaccine against papilloma virus infections. Therefore, the present invention represents a break-through in the field of papilloma virus research.

The invention is explained by the examples. The following preparations and examples are given to enable those skilled in the art to more clearly understand and to practice the present invention. The present invention is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1: Identification of papilloma virus genome VS93-1G

The total DNA is isolated from the biopsy WV-8495 of a squamous-epithelial carcinoma of an immunosuppressed person. 10 $\mu g$ of this DNA are cleaved by the restriction enzyme BamHI and separated electrophoretically in a 0.5% agarose gel. At the same time, 10 $\mu g$ of the above DNA which has not been cleaved are also separated. The result of the electrophoresis is shown in FIG. 10. It follows therefrom that a DNA molecule exists in the non-cleaved DNA in a form typical of an extrachromosomal DNA, i.e. a "supercoiled molecule" and "open circular molecule", respectively. This DNA molecule is cleaved by BamHI into two fragments.

The above agarose gel is subjected to a blotting method whereby the DNA is transferred from the agarose gel to a nitrocellulose membrane. It is used in a hybridization method in which the above DNA of FIG. 1 is employed in combination with the HP virus 29 DNA as $p^{32}$-labeled sample. Hybridization with the above DNA molecule is obtained.

The person skilled in the field of the DNA recombination technique is familiar with the above methods. Reference is made to Sambrook et al., supra, by way of supplement.

B. Example 2: Cloning of the papilloma virus genome VS93-1-G

The DNA, obtained from Example 1, of biopsy WV-8495 is cleaved by the restriction enzyme BamHI. The resulting fragments are inserted in a ligase reaction in which the BamHI-cleaved and dephosphorylated vector ZAP Express is present.

The resulting recombinant DNA molecules are packaged in bacteriophages which are used for infecting bacteria. The ZAP expression vector kit offered by the Stratagene company is used for these steps. The resulting phageplaques are then subjected to a hybridization method in which the $p^{32}$-labeled DNA of FIG. 1, used in Example 1, is employed in combination with the $p^{32}$-labeled HP virus 29 DNA. Hybridization with corresponding phageplaques is obtained. The two BamHI fragments of VS93-1-G are isolated therefrom and inserted in another ligase reaction together with a BamHI-cleaved, dephosphorylated plasmid vector, i.e. pBluescript. The resulting recombinant DNA molecules are used for the transformation of bacteria, i.e. *E. coli*. XI1-Blue. A bacterial clone containing the papilloma virus genome VS93-1-G is identified by restriction cleavages and hybridization with the above DNA samples, respectively. The plasmid of this bacterial clone is referred to as pBlue-VS93-1-G.

All references cited within the body of the instant specification are hereby incorporated by reference in their entirety.

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
    (A) LENGTH: 647 base pairs
    (B) TYPE: nucleic acid
    (C) STRANDEDNESS: double
    (D) TOPOLOGY: linear (ii) MOLECULE TYPE: DNA (ix) FEATURE:
    (A) NAME/KEY: CDS
    (B) LOCATION: 1 .. 645

(xi) SEQUENCE DESCRIPTION: SEQ ID NO: 1:

```
GGT AGA GGA CAG CCA TTA GGC GTG GGG TTA AGT GGA CAC CCT CTG TAT        48
Gly Arg Gly Gln Pro Leu Gly Val Gly Leu Ser Gly His Pro Leu Tyr
 1               5                  10                  15

AAC AAA CTG AAT GAC ACT GAA AAC TCC AAC ATT GCA CAT GCT GAC AAT        96
Asn Lys Leu Asn Asp Thr Glu Asn Ser Asn Ile Ala His Ala Asp Asn
             20                  25                  30

AGT CCT GAC TCC CGG GAC AAC ATT TCT GTT GAC TGT AAG CAA ACA CAA       144
Ser Pro Asp Ser Arg Asp Asn Ile Ser Val Asp Cys Lys Gln Thr Gln
         35                  40                  45

CTG TGC ATA CTG GGC TGT ACG CCC CCC ATG GGG GAA TAC TGG GGT AAG       192
Leu Cys Ile Leu Gly Cys Thr Pro Pro Met Gly Glu Tyr Trp Gly Lys
     50                  55                  60

GGT ACC CCT TGT GCA CGT ACT AAT ACT ACC CCA GGA GAC TGT CCT CCC       240
Gly Thr Pro Cys Ala Arg Thr Asn Thr Thr Pro Gly Asp Cys Pro Pro
 65                  70                  75                  80

TTG GAG TTA ATG ACA TCT TAT ATT CAG GAT GGC GAC ATG GTG GAT ACC       288
Leu Glu Leu Met Thr Ser Tyr Ile Gln Asp Gly Asp Met Val Asp Thr
                 85                  90                  95

GGG TAT GGT GCC ATG GAC TTT ACT GCC CTG CAA TTT AAT AAG TCT GAC       336
Gly Tyr Gly Ala Met Asp Phe Thr Ala Leu Gln Phe Asn Lys Ser Asp
             100                 105                 110

GTG CCC CTT GAT ATT TGC CAG TCT ATT TGC AAA TAT CCC GAT TAT TTG       384
Val Pro Leu Asp Ile Cys Gln Ser Ile Cys Lys Tyr Pro Asp Tyr Leu
         115                 120                 125

GGC ATG GCT GCC GAC CCG TAT GGC GAT AGC ATG TTC TTT TTC CTC CGT       432
Gly Met Ala Ala Asp Pro Tyr Gly Asp Ser Met Phe Phe Phe Leu Arg
     130                 135                 140

CGG GAA CAA CTG TTT GCC AGA CAC TTT TTC AAT CGT GCG GGT GAT GTT       480
Arg Glu Gln Leu Phe Ala Arg His Phe Phe Asn Arg Ala Gly Asp Val
145                 150                 155                 160

GGA GAC AAA ATT CCA GAA TCT TTG TAC CTC AAA GGG AGT AGC GGG CGT       528
Gly Asp Lys Ile Pro Glu Ser Leu Tyr Leu Lys Gly Ser Ser Gly Arg
                 165                 170                 175

GAG ACT CCC GGC AGT GCT ATA TAC AGC CCC ACA CCC AGT GGG TCT ATG       576
Glu Thr Pro Gly Ser Ala Ile Tyr Ser Pro Thr Pro Ser Gly Ser Met
             180                 185                 190

GTG ACC TCT GAG GCA CAA ATA TTC AAT AAG TCT TAC TGG CTA CAG CAA       624
Val Thr Ser Glu Ala Gln Ile Phe Asn Lys Ser Tyr Trp Leu Gln Gln
         195                 200                 205

GCT CAA GGC CAA AAT AAC GGT AT                                        647
Ala Gln Gly Gln Asn Asn Gly
     210                 215
```

(2) INFORMATION FOR SEQ ID NO: 2:

(i) SEQUENCE CHARACTERISTICS:
        (A) LENGTH: 668 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1 .. 666

(xi) SEQUENCE DESCRIPTION: SEQ ID NO: 2:

```
TCA AGA GGA CAC CCA TTA GGA GTA GGG TCT ACA GGT CAT CCC CTA TTT      48
Ser Arg Gly His Pro Leu Gly Val Gly Ser Thr Gly His Pro Leu Phe
 1               5                  10                  15

AAT AAA GTG AAG GAT ACG GAA AAT GCT AAT AAT TAT ATA GTA ACA TCT      96
Asn Lys Val Lys Asp Thr Glu Asn Ala Asn Asn Tyr Ile Val Thr Ser
            20                  25                  30

AAG GAT GAT AGG CAG GAC ACC TCA TTT GAT CCT AAA CAG GTT CAA ATG     144
Lys Asp Asp Arg Gln Asp Thr Ser Phe Asp Pro Lys Gln Val Gln Met
        35                  40                  45

TTT ATT ATT GGC TGC GCA CCG TGC ATA GGT GAG CAC TGG GAT GCA GCC     192
Phe Ile Ile Gly Cys Ala Pro Cys Ile Gly Glu His Trp Asp Ala Ala
    50                  55                  60

AAG CCC TGT GAT GCT GAC AGA GGG GTA GGC AAA TGT CCA CCT TTG GAA     240
Lys Pro Cys Asp Ala Asp Arg Gly Val Gly Lys Cys Pro Pro Leu Glu
65                  70                  75                  80

CTG GTA AAT ACT GTA ATA GAA GAT GGA GAT ATG GTG GAT ATA GGT TTT     288
Leu Val Asn Thr Val Ile Glu Asp Gly Asp Met Val Asp Ile Gly Phe
                85                  90                  95

GGA AAT ATA AAT AAT AAA ACC CTG TCA GCA AAT AAG TCA GAT GTC AGT     336
Gly Asn Ile Asn Asn Lys Thr Leu Ser Ala Asn Lys Ser Asp Val Ser
            100                 105                 110

TTA GAT ATA GTT AAT AAT ATT TGT AAG TAT CCA GAC TTT TTA AAA ATG     384
Leu Asp Ile Val Asn Asn Ile Cys Lys Tyr Pro Asp Phe Leu Lys Met
        115                 120                 125

GCC AAT GAC ATA TAT GGA GAC TCC TGT TTT TTT TAT GCT AGA CGG GAG     432
Ala Asn Asp Ile Tyr Gly Asp Ser Cys Phe Phe Tyr Ala Arg Arg Glu
    130                 135                 140

CAA TGT TAT GCT AGA CAT TTT TTT GTT AGA GGA GGT AAT GTA GGA GAT     480
Gln Cys Tyr Ala Arg His Phe Phe Val Arg Gly Gly Asn Val Gly Asp
145                 150                 155                 160

GCT ATT CCT GAT GCT GCA GTG GGT CAG GAC AAT AAC TTT GTG TTG CCT     528
Ala Ile Pro Asp Ala Ala Val Gly Gln Asp Asn Asn Phe Val Leu Pro
                165                 170                 175

GCA GCT GTT GGA CAG GCC CAA AAC ACT TTG GGT AGC TCT ATT TAC GTG     576
Ala Ala Val Gly Gln Ala Gln Asn Thr Leu Gly Ser Ser Ile Tyr Val
            180                 185                 190

CCT ACC GTT AGT GGT TCT TTG GTA TCC ACA GAT GCA CAA TTA TTT AAT     624
Pro Thr Val Ser Gly Ser Leu Val Ser Thr Asp Ala Gln Leu Phe Asn
        195                 200                 205

AGG CCC TTT TGG CTA CAA CGA GCA CAG GGT CAT AAT AAC GGT AT          668
Arg Pro Phe Trp Leu Gln Arg Ala Gln Gly His Asn Asn Gly
    210                 215                 220
```

(2) INFORMATION FOR SEQ ID NO: 3:

(i) SEQUENCE CHARACTERISTICS:
        (A) LENGTH: 661 base pairs (B) TYPE: nucleic acid
            (C) STRANDEDNESS: double
            (D) TOPOLOGY: linear (ii) MOLECULE TYPE: DNA (ix) FEATURE:
            (A) NAME/KEY: CDS
            (B) LOCATION: 1 .. 660

(xi) SEQUENCE DESCRIPTION: SEQ ID NO: 3:

```
TCT AGG GGG CAA CCC TTG GGG GTA GGT TCT ACA GGC CAT CCT TTG TTC        48
Ser Arg Gly Gln Pro Leu Gly Val Gly Ser Thr Gly His Pro Leu Phe
 1               5                  10                  15

AAT AAA GTA AAG GAT ACT GAA AAT TCA AAT AAT TAT ATA ACA ATG TCT        96
Asn Lys Val Lys Asp Thr Glu Asn Ser Asn Asn Tyr Ile Thr Met Ser
                20                  25                  30

AAA GAT GAT AGG CAG GAC ACC TCG TTT GAC CCT AAG CAG GTT CAA ATG       144
Lys Asp Asp Arg Gln Asp Thr Ser Phe Asp Pro Lys Gln Val Gln Met
            35                  40                  45

TTT ATT ATT GGC TGT GCA CCT TGT ATA GGG GAG CAC TGG GAT GCT GCC       192
Phe Ile Ile Gly Cys Ala Pro Cys Ile Gly Glu His Trp Asp Ala Ala
        50                  55                  60

AAA CCC TGT GAC GCT GAC AAA GGA GAC GGT AAA TGT CCA CCT TTA GAA       240
Lys Pro Cys Asp Ala Asp Lys Gly Asp Gly Lys Cys Pro Pro Leu Glu
 65                  70                  75                  80

TTA GTA AAT ACA GTT ATT GAG GAT GGG GAT ATG GTG GAT ATA GGT TTT       288
Leu Val Asn Thr Val Ile Glu Asp Gly Asp Met Val Asp Ile Gly Phe
                85                  90                  95

GGT AAC ATA AAT AAT AAA ACC TTG TCA GCA AAT AAA TCA GAT GTC AGT       336
Gly Asn Ile Asn Asn Lys Thr Leu Ser Ala Asn Lys Ser Asp Val Ser
            100                 105                 110

TTG GAT ATA GTT AAT AAC ATT TGT AAG TAT CCA GAC TTC CTT AAA ATG       384
Leu Asp Ile Val Asn Asn Ile Cys Lys Tyr Pro Asp Phe Leu Lys Met
        115                 120                 125

GCC AAT GAC ATA TAT GGG GAC TCC TGT TTT TTT TAT GCC AGG CGG GAA       432
Ala Asn Asp Ile Tyr Gly Asp Ser Cys Phe Phe Tyr Ala Arg Arg Glu
130                 135                 140

CAA TGT TAT GCT AGA CAC TTT TTT GTT AGG GGA GGC AAT GTA GGC GAT       480
Gln Cys Tyr Ala Arg His Phe Phe Val Arg Gly Gly Asn Val Gly Asp
145                 150                 155                 160

CGA ATT CCT AAT GCT GCA GTG GGT CAG GAC AAT AAT TTT ATG TTA CCT       528
Arg Ile Pro Asn Ala Ala Val Gly Gln Asp Asn Asn Phe Met Leu Pro
                165                 170                 175

GCA GCC GCT GGG CAG GCT CAA AAC ACT TTG GGC AAC TCT ATT TAT GTT       576
Ala Ala Ala Gly Gln Ala Gln Asn Thr Leu Gly Asn Ser Ile Tyr Val
            180                 185                 190

CCC ACG TCA AGT GGT TCT TTG GTG TCC ACA GAT GCT CAA TTA TTT AAC       624
Pro Thr Val Ser Gly Ser Leu Val Ser Thr Asp Ala Gln Leu Phe Asn
        195                 200                 205

AGG CCA TTT TGG CTG CAA CGA GCA CAA GGT CAC AAC A                     661
Arg Pro Phe Trp Leu Gln Arg Ala Gln Gly His Asn
    210                 215                 220
```

(2) INFORMATION FOR SEQ ID NO: 4:

(i) SEQUENCE CHARACTERISTICS:
            (A) LENGTH: 677 base pairs
            (B) TYPE: nucleic acid
            (C) STRANDEDNESS: double
            (D) TOPOLOGY: linear (ii) MOLECULE TYPE: DNA (ix) FEATURE:
    (A) NAME/KEY: CDS
    (B) LOCATION: 1 .. 675

(xi) SEQUENCE DESCRIPTION: SEQ ID NO: 4:

| | | | | | | | | | | | | | | | | |
|---|---|---|---|---|---|---|---|---|---|---|---|---|---|---|---|---|
| GGA | AGT | GGT | CTT | CCA | TTA | GGC | ATA | GGC | AGC | AGT | GGT | CAC | CCT | CTG | TTT | 48 |
| Gly | Ser | Gly | Leu | Pro | Leu | Gly | Ile | Gly | Ser | Ser | Gly | His | Pro | Leu | Phe | |
| 1 | | | | 5 | | | | | 10 | | | | | 15 | | |
| AAC | AAG | GTA | AAT | GAT | ACA | GAA | AAT | GGC | AAC | ACA | TAT | AAA | GGG | ACA | ACT | 96 |
| Asn | Lys | Val | Asn | Asp | Thr | Glu | Asn | Gly | Asn | Thr | Tyr | Lys | Gly | Thr | Thr | |
| | | | 20 | | | | | 25 | | | | | 30 | | | |
| AAA | GAT | GAT | AGA | CAA | AAC | ATT | TCA | TTT | GAT | CCT | AAA | CAA | TTA | CAG | ATG | 144 |
| Lys | Asp | Asp | Arg | Gln | Asn | Ile | Ser | Phe | Asp | Pro | Lys | Gln | Leu | Gln | Met | |
| | | 35 | | | | | 40 | | | | | 45 | | | | |
| TTT | ATA | ATT | GGC | TGT | ACA | CCA | TGT | ATT | GGT | GAA | CAT | TGG | GAT | AAG | GCT | 192 |
| Phe | Ile | Ile | Gly | Cys | Thr | Pro | Cys | Ile | Gly | Glu | His | Trp | Asp | Lys | Ala | |
| 50 | | | | | 55 | | | | | 60 | | | | | | |
| CCT | GCA | TGT | GTT | AAT | GAT | ATT | CAA | CAA | GGT | AGT | TGC | CCA | CCA | ATA | GAA | 240 |
| Pro | Ala | Lys | Val | Asn | Asp | Ile | Gln | Gln | Gly | Ser | Cys | Pro | Pro | Ile | Glu | |
| 65 | | | | 70 | | | | | 75 | | | | | 80 | | |
| TTA | GTT | AAC | ACA | TAC | ATA | CAG | GGT | GGA | GAT | ATG | GCT | GAT | ATA | GGA | TAT | 288 |
| Leu | Val | Asn | Thr | Tyr | Ile | Gln | Gly | Gly | Asp | Met | Ala | Asp | Ile | Gly | Tyr | |
| | | | 85 | | | | | 90 | | | | | 95 | | | |
| GGC | AAT | CTA | AAT | TTT | AAA | GCT | TTA | CAG | CAA | AAT | AGA | TCA | GAT | GTT | AGC | 336 |
| Gly | Asn | Leu | Asn | Phe | Lys | Ala | Leu | Gln | Gln | Asn | Arg | Ser | Asp | Val | Ser | |
| | | 100 | | | | | 105 | | | | | 110 | | | | |
| TTG | GAT | ATT | GTA | GAT | GAA | ATA | TGC | AAA | TAT | CCT | GAC | TTT | TTA | CGA | ATG | 384 |
| Leu | Asp | Ile | Val | Asp | Glu | Ile | Cys | Lys | Tyr | Pro | Asp | Phe | Leu | Arg | Met | |
| | | 115 | | | | | 120 | | | | | 125 | | | | |
| CAA | AAT | GAT | GTA | TAT | GGC | GAT | GCC | TGT | TTT | TTT | TAT | GCT | CGA | CGG | GAG | 432 |
| Gln | Asn | Asp | Val | Tyr | Gly | Asp | Ala | Cys | Phe | Phe | Tyr | Ala | Arg | Arg | Glu | |
| 130 | | | | | 135 | | | | | 140 | | | | | | |
| CAA | TGT | TAT | GCC | AGG | CAC | TTT | TTT | GTG | CGT | GGT | GGC | AAA | CCT | GGT | GAT | 480 |
| Gln | Cys | Tyr | Ala | Arg | His | Phe | Phe | Val | Arg | Gly | Gly | Lys | Pro | Gly | Asp | |
| 145 | | | | | 150 | | | | | 155 | | | | | 160 | |
| GAT | ATA | CCT | GGT | GCC | CAA | ATT | GAT | GCA | GGG | TCA | CAT | AAA | AAT | GAA | TAT | 528 |
| Asp | Ile | Pro | Gly | Ala | Gln | Ile | Asp | Ala | Gly | Ser | His | Lys | Asn | Glu | Tyr | |
| | | | | 165 | | | | | 170 | | | | | 175 | | |
| TAC | ATA | CAG | GCA | GCT | TCA | GAC | CAA | TCA | CAA | AAT | AGT | TTG | GGG | AAT | TCT | 576 |
| Tyr | Ile | Gln | Ala | Ala | Ser | Asp | Gln | Ser | Gln | Asn | Ser | Leu | Gly | Asn | Ser | |
| | | | 180 | | | | | 185 | | | | | 190 | | | |
| ATG | TAT | TTC | CCA | ACT | ATC | AGT | GGC | TCA | TTA | GTT | TCA | AGT | GAT | GCT | CAA | 624 |
| Met | Tyr | Phe | Pro | Thr | Ile | Ser | Gly | Ser | Leu | Val | Ser | Ser | Asp | Ala | Gln | |
| | | | 195 | | | | | 200 | | | | | 205 | | | |
| TTA | TTT | AAT | AGG | CCC | TTC | TGG | CTA | CAG | CGA | GCA | CAA | GGC | CAA | AAC | AAC | 672 |
| Leu | Phe | Asn | Arg | Pro | Phe | Trp | Leu | Gln | Arg | Ala | Gln | Gly | Gln | Asn | Asn | |
| | | 210 | | | | | 215 | | | | | 220 | | | | |
| GGG | AT | | | | | | | | | | | | | | | 677 |
| Gly | | | | | | | | | | | | | | | | |
| 225 | | | | | | | | | | | | | | | | |

(2) INFORMATION FOR SEQ ID NO: 5:

(i) SEQUENCE CHARACTERISTICS:
    (A) LENGTH: 674 base pairs
    (B) TYPE: nucleic acid
    (C) STRANDEDNESS: double
    (D) TOPOLOGY: linear (ii) MOLECULE TYPE: DNA (ix) FEATURE:
    (A) NAME/KEY: CDS (B) LOCATION: 1 .. 672

(xi) SEQUENCE DESCRIPTION: SEQ ID NO: 5:

```
TCA AGG GGA CAG CCA TTG GGT GTA GGA ACA TCA GGT CAT CCT TTA TTT      48
Ser Arg Gly Gln Pro Leu Gly Val Gly Thr Ser Gly His Pro Leu Phe
1               5                   10                  15

AAC AAA GTC AGG GAT ACT GAA AAC TCA GGT AAC TAT CAA GCA GTT TCT      96
Asn Lys Val Arg Asp Thr Glu Asn Ser Gly Asn Tyr Gln Ala Val Ser
            20                  25                  30

CAG GAT GAC AGA CAA AAT ACA TCT TTT GAT CCT AAA CAA GTG CAA ATG     144
Gln Asp Asp Arg Gln Asn Thr Ser Phe Asp Pro Lys Gln Val Gln Met
35                  40                  45

TTT GTC ATT GGC TGT GTG CCG TGT ATG GGT GAA CAT TGG GAC AAA GCT     192
Phe Val Ile Gly Cys Val Pro Cys Met Gly Glu His Trp Asp Lys Ala
        50                  55                  60

AAG GTT TGT GAA TCA GAA GCA AAT AAT CAA CAA GGC TTA TGT CCA CCC     240
Lys Val Cys Glu Ser Glu Ala Asn Asn Gln Gln Gly Leu Cys Pro Pro
65                  70                  75                  80

ATA GAG TTA AAA AAT TCA GTA ATT GAA GAT GGA GAT ATG TTT GAT ATA     288
Ile Glu Leu Lys Asn Ser Val Ile Glu Asp Gly Asp Met Phe Asp Ile
                85                  90                  95

GGC TTT GGA AAT ATT AAT AAC AAA GCA CTA TCT TAT AAC AAG TCA GAT     336
Gly Phe Gly Asn Ile Asn Asn Lys Ala Leu Ser Tyr Asn Lys Ser Asp
            100                 105                 110

GTT AGT TTA GAT ATA GTT AAT GAA GTG TGC AAA TAT CCA GAC TTT TTA     384
Val Ser Leu Asp Ile Val Asn Glu Val Cys Lys Tyr Pro Asp Phe Leu
        115                 120                 125

ACC ATG GCT AAT GAT GTG TAT GGA GAT GCT TGT TTT TTC TTT GCT AGA     432
Thr Met Ala Asn Asp Val Tyr Gly Asp Ala Cys Phe Phe Phe Ala Arg
130                 135                 140

CGA GAA CAA TGT TAT GCC AGA CAT TAT TTT GTT AGG GGA GGC AAT GTT     480
Arg Glu Gln Cys Tyr Ala Arg His Tyr Phe Val Arg Gly Gly Asn Val
145                 150                 155                 160

GGC GAT GCA ATC CCT GAT GGA GCA GTA CAA CAG GAT CAC AAC TAT TAT     528
Gly Asp Ala Ile Pro Asp Gly Ala Val Gln Gln Asp His Asn Tyr Tyr
                165                 170                 175

TTA CCT GCA CAA AAT GCA CAG CAA CAA CAC ACC TTG GGA AAT TCT ATA     576
Leu Pro Ala Gln Asn Ala Gln Gln Gln His Thr Leu Gly Asn Ser Ile
            180                 185                 190

TAT TAT CCA ACT GTT AGT GGG TCT CTT GTA ACA TCT GAT GCT CAG TTA     624
Tyr Tyr Pro Thr Val Ser Gly Ser Leu Val Thr Ser Asp Ala Gln Leu
        195                 200                 205

TTT AAT AGA CCA TTT TGG TTA CAA CGT GCT CAA GGA CAA AAC AAC GGT     672
Phe Asn Arg Pro Phe Trp Leu Gln Arg Ala Gln Gly Gln Asn Asn Gly
210                 215                 220

AT                                                                  674
```

(2) INFORMATION FOR SEQ ID NO: 6:

(i) SEQUENCE CHARACTERISTICS:
        (A) LENGTH: 662 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1 .. 660

(xi) SEQUENCE DESCRIPTION: SEQ ID NO: 6:

```
GGT AGT GGG CAA CCA TTA GGT GTA GGC ACC ACA GGA CAT CCA CTG TTT      48
Gly Ser Gly Gln Pro Leu Gly Val Gly Thr Thr Gly His Pro Leu Phe
 1               5                  10                  15

AAT AAA CTT AGA GAT TCA GAA AAT TCT GCA GAA CGT CTG GAA GGA ACA      96
Asn Lys Leu Arg Asp Ser Glu Asn Ser Ala Glu Arg Leu Glu Gly Thr
             20                  25                  30

AGT GAT GAT AGG AGG AAT ATA TCA TTT GAT CCT AAG CAA GTG CAA ATG     144
Ser Asp Asp Arg Arg Asn Ile Ser Phe Asp Pro Lys Gln Val Gln Met
 35                  40                  45

TTT GTG ATA GGC TGC ACC CCC TGT TTA GGG GAG TAT TGG GAT ACA GCT     192
Phe Val Ile Gly Cys Thr Pro Cys Leu Gly Glu Tyr Trp Asp Thr Ala
         50                  55                  60

CCA GTA TGT AAA GAT GCA GGA AGT CAA TTA GGC CTT TGC CCT CCA TTA     240
Pro Val Cys Lys Asp Ala Gly Ser Gln Leu Gly Leu Cys Pro Pro Leu
 65                  70                  75                  80

GAA TTA AAA AAC AGT GTT ATA GAA GAT GGC GAT ATG TTT GAT ATA GGA     288
Glu Leu Lys Asn Ser Val Ile Glu Asp Gly Asp Met Phe Asp Ile Gly
                 85                  90                  95

TTT GGC AAT ATT AAC AAC AAA ACA TTA AGT TTT AAT AAG TCA GAT GTT     336
Phe Gly Asn Ile Asn Asn Lys Thr Leu Ser Phe Asn Lys Ser Asp Val
            100                 105                 110

AGT GTG GAC ATT GTT AAT GAA ATT TGT AAA TAT CCT GAT TTT TTA ACT     384
Ser Val Asp Ile Val Asn Glu Ile Cys Lys Tyr Pro Asp Phe Leu Thr
        115                 120                 125

ATG TCC AAT GAT GTT TAT GGA GAC TCT TGC TTT TTC TTT GCT CGC AGA     432
Met Ser Asn Asp Val Tyr Gly Asp Ser Cys Phe Phe Phe Ala Arg Arg
130                 135                 140

GAG CGA TGT TAT GCA AGG CAT TAT TTT GTA CGC GGA GGG GCA GTG GGT     480
Glu Arg Cys Tyr Ala Arg His Tyr Phe Val Arg Gly Gly Ala Val Gly
145                 150                 155                 160

GAT TTA ATA CCA GAT GCT ACA GTT AAT CAG GAC CAT AAA TAT TAC TTA     528
Asp Leu Ile Pro Asp Ala Thr Val Asn Gln Asp His Lys Tyr Tyr Leu
                165                 170                 175

CCA GCA AAT CCA CCT GCC ACA TTG GAA AAC TCT ACA TAC TTT CCG ACT     576
Pro Ala Asn Pro Pro Ala Thr Leu Glu Asn Ser Thr Tyr Phe Pro Thr
            180                 185                 190

GCT AGT GGC TCC TTA GTG ACA TCT GAT GCA CAA TTA TTT AAT AGG CCC     624
Ala Ser Gly Ser Leu Val Thr Ser Asp Ala Gln Leu Phe Asn Arg Pro
        195                 200                 205

TTT TGG TTA AAA CGT GCA CAA GGT CAT AAT AAT GGT AT                  662
Phe Trp Leu Lys Arg Ala Gln Gly His Asn Asn Gly
210                 215                 220

(2) INFORMATION FOR SEQ ID NO: 7:

(i) SEQUENCE CHARACTERISTICS:
        (A) LENGTH: 665 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1 .. 663

(xi) SEQUENCE DESCRIPTION: SEQ ID NO: 7:

GGT AGG GGG CAA CCA TTT GGG GTA GGC ACT ACA GGT CAT CCA TTA TTT      48
Gly Arg Gly Gln Pro Phe Gly Val Gly Thr Thr Gly His Pro Leu Phe
 1               5                  10                  15

AAC AAA TTA CGT GAT GCA GAA AAT TCC AGC GAA CGT CAG GGA GAT ACT      96
Asn Lys Leu Arg Asp Ala Glu Asn Ser Ser Glu Arg Gln Gly Asp Thr
```

```
GCT GCA GAT GAC AGA ATG AAT ATA TCT TTT GAT CCT AAG CAG GTA CAA    144
Ala Ala Asp Asp Arg Met Asn Ile Ser Phe Asp Pro Lys Gln Val Gln
         35                  40                  45

ATG TTC ATA ATA GGT TGC ACA CCG TGT TTA GGT GAA TAT TGG GAT CAA    192
Met Phe Ile Ile Gly Cys Thr Pro Cys Leu Gly Glu Tyr Trp Asp Gln
     50                  55                  60

GCG CCT GTA TGT AAA GAT GCA GGT AAC CAA ATG GGC TTA TGT CCT CCT    240
Ala Pro Val Cys Lys Asp Ala Gly Asn Gln Met Gly Leu Cys Pro Pro
 65                  70                  75                  80

CTT GAA CTA AAG AAT AGT GTC ATA GAA GAT GGA GAT ATG TTT GAT ATA    288
Leu Glu Leu Lys Asn Ser Val Ile Glu Asp Gly Asp Met Phe Asp Ile
                 85                  90                  95

GGC TTT GGT AAC ATT AAT AAT AAG ACA CTG TCA TTC AAT AGA TCA GAT    336
Gly Phe Gly Asn Ile Asn Asn Lys Thr Leu Ser Phe Asn Arg Ser Asp
            100                 105                 110

GTT AGT TTA GAT ATT GTA AAT GAA ATA TGC AAA TAT CCA GAT TTT TTA    384
Val Ser Leu Asp Ile Val Asn Glu Ile Cys Lys Tyr Pro Asp Phe Leu
        115                 120                 125

ACA ATG TCC AAT GAT GTT TAT GGT GAC TCC TGT TTT TTT TGT GCT CGA    432
Thr Met Ser Asn Asp Val Tyr Gly Asp Ser Cys Phe Phe Cys Ala Arg
    130                 135                 140

AGA GAG CAA TGT TAT GCT AGA CAT TAT TTT GTA CGA GGC GGT GTT GTT    480
Arg Glu Gln Cys Tyr Ala Arg His Tyr Phe Val Arg Gly Gly Val Val
145                 150                 155                 160

GGA GAT TCT ATA CCA GAC GGT GCA GTC CAG CAG AGT AAC AAA TAT TAT    528
Gly Asp Ser Ile Pro Asp Gly Ala Val Gln Gln Ser Asn Lys Tyr Tyr
                165                 170                 175

TTA GCT TCA GCT CAA AAT AAT AGC TTG GAA AAT TCT ACC TAT TTC CCA    576
Leu Ala Ser Ala Gln Asn Asn Ser Leu Glu Asn Ser Thr Tyr Phe Pro
            180                 185                 190

ACT GTA AGT GGT TCT TTA GTG ACT TCT GAT GCT CAG CTA TTT AAC AGA    624
Thr Val Ser Gly Ser Leu Val Thr Ser Asp Ala Gln Leu Phe Asn Arg
        195                 200                 205

CCC TTT TGG TTA AAG CGT GCT CAA GGG CAT AAT AAT GGA AT             665
Pro Phe Trp Leu Lys Arg Ala Gln Gly His Asn Asn Gly
    210                 215                 220
```

(2) INFORMATION FOR SEQ ID NO: 8:

(i) SEQUENCE CHARACTERISTICS:
       (A) LENGTH: 674 base pairs
       (B) TYPE: nucleic acid
       (C) STRANDEDNESS: double
       (D) TOPOLOGY: linear (ii) MOLECULE TYPE: DNA (ix) FEATURE:
       (A) NAME/KEY: CDS
       (B) LOCATION: 1 .. 672

(xi) SEQUENCE DESCRIPTION: SEQ ID NO: 8:

```
GGA AGA GGT CTC CAT TTG GGT GTA GGT ACA GCA GGC CAT CCA CTA TTC     48
Gly Arg Gly Leu His Leu Gly Val Gly Thr Ala Gly His Pro Leu Phe
 1               5                  10                  15

AAT AAA GTT AGA GAT ACA GAA AAT AAT AGT GGC TAT CAA GAT ACG TCT     96
Asn Lys Val Arg Asp Thr Glu Asn Asn Ser Gly Tyr Gln Asp Thr Ser
                 20                  25                  30

ACG GAT GAC AGA CAA AAT ACA TCA TTT GAT CCA AAA CAA GTT CAA ATG    144
Thr Asp Asp Arg Gln Asn Thr Ser Phe Asp Pro Lys Gln Val Gln Met
         35                  40                  45
```

```
TTT GTA GTA GGA TGT GCT CCT TGT TTG GGA GAA CAT TGG GAT AAA GCT      192
Phe Val Val Gly Cys Ala Pro Cys Leu Gly Glu His Trp Asp Lys Ala
     50                  55                  60

CCT GTC TGT GAC TCA GAT AAA AAT AAC CAG GCT GGA AAA TGC CCT CCA      240
Pro Val Cys Asp Ser Asp Lys Asn Asn Gln Ala Gly Lys Cys Pro Pro
 65                  70                  75                  80

TTA GAA CTG AGA AAC ACA GTA ATA GAA GAT GGA GAT ATG ATT GAT ATA      288
Leu Glu Leu Arg Asn Thr Val Ile Glu Asp Gly Asp Met Ile Asp Ile
                 85                  90                  95

GGC TTT GGC AAT ATA AAC AAC AAG GTT TTA TCA GTT ACT AAG TCA GAT      336
Gly Phe Gly Asn Ile Asn Asn Lys Val Leu Ser Val Thr Lys Ser Asp
                100                 105                 110

GTT AGT CTG GAT ATA GTT AAT GAA ACT TGT AAG TAT CCA GAT TTT TTA      384
Val Ser Leu Asp Ile Val Asn Glu Thr Cys Lys Tyr Pro Asp Phe Leu
115                 120                 125

ACT ATG GCC AAT GAT GTA TAT GGT GAC TCT TGT TTT TTC TTT GCA AGG      432
Thr Met Ala Asn Asp Val Tyr Gly Asp Ser Cys Phe Phe Phe Ala Arg
        130                 135                 140

AGA GAA CAG TGT TAT GCT AGA CAT TAT TAT GTT AGG GGA GGT GTA GTA      480
Arg Glu Gln Cys Tyr Ala Arg His Tyr Tyr Val Arg Gly Gly Val Val
145                 150                 155                 160

GGT GAT GCT ATT CCT GAT GAA GCT GTG AAT CAA GAT AAA AAC TTT GTG      528
Gly Asp Ala Ile Pro Asp Glu Ala Val Asn Gln Asp Lys Asn Phe Val
                165                 170                 175

TTA CCT GCA CAA GGC ACT CAG CAA CAA AAG GAT ATA GCT AGT TCT ATA      576
Leu Pro Ala Gln Gly Thr Gln Gln Gln Lys Asp Ile Ala Ser Ser Ile
                180                 185                 190

TAT TTT CCA ACT GTT AGT GGT TCC TTA GTA ACT TCT GAT GCT CAA TTA      624
Tyr Phe Pro Thr Val Ser Gly Ser Leu Val Thr Ser Asp Ala Gln Leu
        195                 200                 205

TTT AAC AGA CCA TTT TGG TTA CGC AGA GCA CAA GGG CAA AAT AAC GGG      672
Phe Asn Arg Pro Phe Trp Leu Arg Arg Ala Gln Gly Gln Asn Asn Gly
210                 215                 220

AT                                                                   674

(2) INFORMATION FOR SEQ ID NO: 9:

(i) SEQUENCE CHARACTERISTICS:
        (A) LENGTH: 686 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1 .. 684

(xi) SEQUENCE DESCRIPTION: SEQ ID NO: 9:

GGG AGA GGA CAG CCA TTA GGC GTT GGT ACC AGT GGA CAT CCA CTG TTT       48
Gly Arg Gly Gln Pro Leu Gly Val Gly Thr Ser Gly His Pro Leu Phe
 1                5                  10                  15

AAC AAA GTT AAT GAT GCC GAA AAT CCC TTA GCT TAC AGG GCA CAG GCC       96
Asn Lys Val Asn Asp Ala Glu Asn Pro Leu Ala Tyr Arg Ala Gln Ala
                 20                  25                  30

TTT TCT ACT GAT GAT AGG CAA AAC ACA TCC TTT GAT CCT AAA CAA ATA      144
Phe Ser Thr Asp Asp Arg Gln Asn Thr Ser Phe Asp Pro Lys Gln Ile
             35                  40                  45

CAA ATG TTT ATA ATA GGT TGT GCA CCC TGT ATT GGA GAG CAT TGG GAT      192
Gln Met Phe Ile Ile Gly Cys Ala Pro Cys Ile Gly Glu His Trp Asp
         50                  55                  60
```

-continued

```
GTA GGT GAA CGT TGT GCA GGA GCC AAT AAT GAA AAT GGT CGA TGC CCC        240
Val Gly Glu Arg Cys Ala Gly Ala Asn Asn Glu Asn Gly Arg Cys Pro
 65              70                  75                  80

CCT ATT AAA TTG GTA AAT TCA GTC ATC CAA GAT GGA GAT ATG GCA GAT        288
Pro Ile Lys Leu Val Asn Ser Val Ile Gln Asp Gly Asp Met Ala Asp
             85                  90                  95

ATT GGT TAT GGA AAC CTA AAT TTC CGT ACC TTA CAG GAA AAC AGA TCT        336
Ile Gly Tyr Gly Asn Leu Asn Phe Arg Thr Leu Gln Glu Asn Arg Ser
            100                 105                 110

GAT GTA AGT TTA GAT ATA GTG AAT GAA ACC TGT AAA TAT CCA GAC TTT        384
Asp Val Ser Leu Asp Ile Val Asn Glu Thr Cys Lys Tyr Pro Asp Phe
            115                 120                 125

TTA AAG ATG CAG AAT GAT ATA TAT GGC GAT TCT TGC TTT TTC TTT GCT        432
Leu Lys Met Gln Asn Asp Ile Tyr Gly Asp Ser Cys Phe Phe Phe Ala
        130                 135                 140

CGC CGG GAG CAA TGT TAT GCA AGA CAT TTT TTT GTT CGT GGG GGT AAG        480
Arg Arg Glu Gln Cys Tyr Ala Arg His Phe Phe Val Arg Gly Gly Lys
145                 150                 155                 160

GCG GGG GAT GAC ATT CCT GGT GCG CAA ATC GAT GCA GGT ACA TAT AAA        528
Ala Gly Asp Asp Ile Pro Gly Ala Gln Ile Asp Ala Gly Thr Tyr Lys
                165                 170                 175

AAT GAT TTT TAC ATA CCT GGA GCG TCA GGT CAG ACA CAA AAG AAT ATA        576
Asn Asp Phe Tyr Ile Pro Gly Ala Ser Gly Gln Thr Gln Lys Asn Ile
            180                 185                 190

GGT AAC TCG ATG TAT TTC CCA ACA GTA AGT GGC TCA TTG GTG TCT AGT        624
Gly Asn Ser Met Tyr Phe Pro Thr Val Ser Gly Ser Leu Val Ser Ser
        195                 200                 205

GAT GCT CAA TTG TTT AAT AGG CCC TTC TGG CTC CAA CGG GCG CAG GGG        672
Asp Ala Gln Leu Phe Asn Arg Pro Phe Trp Leu Gln Arg Ala Gln Gly
    210                 215                 220

CAA AAC AAC GGA AT                                                     686
Gln Asn Asn Gly
225
```

What is claimed is:

1. An isolated DNA encoding a peptide an L1 papilloma virus major capsid protein, wherein said peptide comprises the amino acid sequence of FIG. 2 (SEQ ID NO: 2), FIG. 3 (SEQ ID NO: 3), FIG. 4 (SEQ ID NO: 4) FIG. 5 (SEQ ID NO: 5), FIG. 6 (SEQ ID NO: 6), FIG. 7 (SEQ ID NO: 7), FIG. 8 (SEQ ID NO: 8), or FIG. 9 (SEQ ID NO: 9).

2. An isolated DNA encoding an L1 papilloma virus major capsid protein, wherein said L1 polypeptide comprises the amino acid sequence of FIG. 1 (SEQ ID NO: 1), FIG. 2 (SEQ ID NO: 2), FIG. 3 (SEQ ID NO: 3), FIG. 4 (SEQ ID NO: 4), FIG. 5 (SEQ ID NO: 5), FIG. 6 (SEQ ID NO: 6), FIG. 7 (SEQ ID NO: 7), FIG. 8 (SEQ ID NO: 8), or FIG. 9 (SEQ ID NO: 9).

3. The isolated DNA of claim 1, wherein said DNA comprises the base sequence of FIG. 2 (SEQ ID NO: 2), FIG. 3 (SEQ ID NO: 3), FIG. 4 (SEQ ID NO: 4), FIG. 5 (SEQ ID NO: 5), FIG. 6 (SEQ ID NO: 6), FIG. 7 (SEQ ID NO: 7), FIG. 8 (SEQ ID NO: 8), or FIG. 9 (SEQ ID NO: 9), or the complement thereof.

4. The isolated DNA of claim 2, wherein the DNA encoding said L1 papilloma virus major capsid protein comprises the base sequence of FIG. 1 (SEQ ID NO: 1), FIG. 2 (SEQ ID NO: 2), FIG. 3 (SEQ ID NO: 3), FIG. 4 (SEQ ID NO: 4), FIG. 5 (SEQ ID NO: 5), FIG. 6 (SEQ ID NO: 6), FIG. 7 (SEQ ID NO: 7), FIG. 8 (SEQ ID NO: 8), or FIG. 9 (SEQ ID NO: 9).

5. A composition comprising the DNA of claim 1, 2, 3, or 4 as reagent for diagnosis.

6. An expression vector, comprising the DNA of claim 1, 2, 3, or 4.

7. A transformant, comprising the expression vector of claim 6.

8. A protein encoded by the DNA of claim 1, 2, 3, or 4.

9. The protein of claim 8, wherein the protein is a L1 papilloma virus major capsid protein.

10. The protein of claim 8, wherein the protein is a papilloma virus minor capsid protein.

11. A virus-like particle, comprising the L1 papilloma virus major capsid protein of claim 9.

12. The virus-like particle of claim 11, comprising additional a papilloma virus minor capsid protein.

13. A composition comprising the protein of claim 8 as reagent for diagnosis, treatment and/or vaccination.

14. A composition comprising the virus-like particle of claim 11 as reagent for diagnosis, treatment and/or vaccination.

15. A pharmaceutical composition comprising the protein of claim 8, and a pharmaceutically acceptable carrier.

16. A composition comprising the virus-like particle of claim 12 as reagent for diagnosis, treatment and/or vaccination.

17. A pharmaceutical composition comprising the virus-like particle of claim 12, and a pharmaceutically acceptable carrier.

18. An antibody, directed against the protein of claim 8.

19. An antibody, directed against the virus-like particle of claim 11.

20. A pharmaceutical composition comprising the antibody of claim 18, and a pharmaceutically acceptable carrier.

21. A composition comprising the antibody of claim 18 as reagent for diagnosis and/or treatment.

22. A composition comprising the antibody of claim 19 as reagent for diagnosis and/or treatment.

23. A pharmaceutical composition comprising the antibody of claim 19, and a pharmaceutically acceptable carrier.

24. A method of producing a DNA sequence comprising a nucleotide sequence encoding an L1 papilloma virus major capsid protein, comprising:

(a) isolating the total DNA from a biopsy of epithelial neoplasm, (b) hybridizing under stringent conditions the total DNA of (a) with a DNA of claim 1, 2, 3, or 4 thereby detecting a papilloma virus genome included in the total DNA of (a), and (c) cloning the total DNA of (a), including the papilloma virus genome, in a vector and optionally subcloning the resulting clone, all of the steps originating from the conventional DNA recombination technique.

25. A method of producing the protein of claim 8, comprising the cultivation of the transformant containing an expression vector encoding said protein under suitable conditions.

26. A method of detecting a papilloma virus DNA, comprising:

(a) hybridizing under stringent conditions the DNA of claim 1, 2, 3, or 4 to a DNA sample; and (b) identifying papilloma virus in said DNA sample by detecting a hybridization signal.

27. A pharmaceutical composition comprising the virus-like particle of claim 11, and a pharmaceutically acceptable carrier.

* * * * *